US008431566B2

(12) United States Patent
Castro et al.

(10) Patent No.: US 8,431,566 B2
(45) Date of Patent: *Apr. 30, 2013

(54) CYCLOPAMINE LACTAM ANALOGS AND METHODS OF USE THEREOF

(75) Inventors: Alfredo Castro, Winchester, MA (US); Michael J. Grogan, Winchester, MA (US); Andre Lescarbeau, Somerville, MA (US); Martin Tremblay, Melrose, MA (US)

(73) Assignee: Infinity Discovery, Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/250,080

(22) Filed: Sep. 30, 2011

(65) Prior Publication Data
US 2012/0083484 A1    Apr. 5, 2012

Related U.S. Application Data

(60) Continuation of application No. 13/102,395, filed on May 6, 2011, now Pat. No. 8,293,760, which is a division of application No. 12/044,878, filed on Mar. 7, 2008, now Pat. No. 7,964, 590.

(60) Provisional application No. 60/893,591, filed on Mar. 7, 2007.

(51) Int. Cl.
*A61K 31/55* (2006.01)
*C07D 491/20* (2006.01)

(52) U.S. Cl.
USPC .......................................... 514/215; 540/521

(58) Field of Classification Search .................. 514/215; 540/521
See application file for complete search history.

(56) References Cited

U.S. PATENT DOCUMENTS

| | | | |
|---|---|---|---|
| 6,177,407 B1 | 1/2001 | Rodgers et al. |
| 6,238,876 B1 | 5/2001 | Altaba |
| 6,291,516 B1 | 9/2001 | Dudek et al. |
| 6,432,970 B2 | 8/2002 | Beachy et al. |
| 6,686,388 B2 | 2/2004 | Dudek et al. |
| 6,867,216 B1 | 3/2005 | Beachy et al. |
| 7,098,196 B1 | 8/2006 | Beachy et al. |
| 7,230,004 B2 | 6/2007 | Adams et al. |
| 7,291,626 B1 | 11/2007 | Beachy et al. |
| 7,407,967 B2 | 8/2008 | Adams et al. |
| 7,476,661 B2 | 1/2009 | Beachy et al. |
| 7,605,167 B2 | 10/2009 | Tas et al. |
| 7,629,352 B2 | 12/2009 | Tas et al. |
| 7,648,994 B2 | 1/2010 | Castro et al. |
| 7,812,164 B2 | 10/2010 | Austad et al. |
| 7,867,492 B2 | 1/2011 | Beachy et al. |
| 7,875,628 B2 | 1/2011 | Adams et al. |
| 7,893,078 B2 | 2/2011 | Tas et al. |
| 7,964,590 B2 | 6/2011 | Castro et al. |
| 7,994,191 B2 | 8/2011 | Castro et al. |
| 8,017,648 B2 | 9/2011 | Castro et al. |
| 2003/0114393 A1 | 6/2003 | Liscovitch et al. |
| 2003/0162870 A1 | 8/2003 | Kimura et al. |
| 2003/0175355 A1 | 9/2003 | Tobyn et al. |
| 2004/0072913 A1 | 4/2004 | Tas et al. |
| 2004/0072914 A1 | 4/2004 | Tas et al. |
| 2004/0110663 A1 | 6/2004 | Dudek et al. |
| 2004/0126359 A1 | 7/2004 | Lamb et al. |
| 2004/0127474 A1 | 7/2004 | Dudek et al. |
| 2006/0094660 A1 | 5/2006 | Thomson |
| 2006/0128639 A1 | 6/2006 | Beachy |
| 2006/0142245 A1 | 6/2006 | Beachy et al. |
| 2007/0009530 A1 | 1/2007 | Altaba |
| 2007/0191410 A1 | 8/2007 | Adams et al. |
| 2007/0231828 A1 | 10/2007 | Beachy et al. |
| 2007/0281040 A1 | 12/2007 | Weichselbaum et al. |
| 2008/0019961 A1 | 1/2008 | Wicha et al. |
| 2008/0057071 A1 | 3/2008 | Watkins et al. |
| 2008/0058298 A1 | 3/2008 | Beachy et al. |
| 2008/0089915 A1 | 4/2008 | Tas et al. |
| 2008/0095761 A1 | 4/2008 | Beachy et al. |
| 2008/0118493 A1 | 5/2008 | Beachy et al. |
| 2008/0255059 A1 | 10/2008 | Beachy et al. |
| 2008/0269272 A1 | 10/2008 | Adams et al. |
| 2008/0293754 A1 | 11/2008 | Austad et al. |
| 2009/0012109 A1 | 1/2009 | Austad et al. |
| 2009/0208579 A1 | 8/2009 | Ueki et al. |
| 2009/0216022 A1 | 8/2009 | Austad et al. |
| 2009/0286822 A1 | 11/2009 | Tas et al. |
| 2010/0003728 A1 | 1/2010 | Jayatilake et al. |
| 2010/0144775 A1 | 6/2010 | Castro et al. |
| 2010/0273818 A1 | 10/2010 | Beachy et al. |
| 2010/0286180 A1 | 11/2010 | Castro et al. |
| 2011/0104254 A1 | 5/2011 | Tas et al. |
| 2011/0166353 A1 | 7/2011 | Adams et al. |
| 2011/0230509 A1 | 9/2011 | Castro et al. |

FOREIGN PATENT DOCUMENTS

| | | |
|---|---|---|
| EP | 0388188 | 9/1990 |
| WO | WO-95/18856 | 7/1995 |
| WO | WO-96/17924 | 5/1996 |
| WO | WO-00/41545 | 7/2000 |

(Continued)

OTHER PUBLICATIONS

Aboulkassim, Tahar O. et al., "Alteration of the PATCHED locus in Superficial Bladder Cancer", Oncogene, vol. 22, (2003), pp. 2967-2971.

Bar, Elis E et al., "Cyclopamine-Mediated Hedgehog Pathway Inhibition Depletes Stem-Like Cancer Cells in Gliobastoma", Stem Cells, vol. 25, (2007), pp. 2524-2533.

Bhattacharya, Resham et al., "Role of Hedgehog Signaling in Ovarian Cancer", Clin. Cancer Research, vol. 14, No. 23, (2008), pp. 7659-7666.

Clement, Virginie et al., "Hedgehod-GLI1 Signaling Regulates Human Glioma Growth, Cancer Stem Cell Self-Renewal and Tumorigenicity", Current Biology, vol. 17, (2007), pp. 1-8.

Cutcliffe, Colleen et al., Clear Cell Sarcoma of the Kidney: Up-regulation of Neural Markers with Activation of the Sonic Hedgehog and Akt Pathways, Human Cancer Biology, vol. 11, No. 22, (2005), pp. 7986-7994.

(Continued)

*Primary Examiner* — Charanjit Aulakh
(74) *Attorney, Agent, or Firm* — Fish & Richardson P.C.

(57) ABSTRACT

The present invention relates to steroidal alkaloids useful in the treatment of hedgehog pathway related disorders, particularly cancer.

23 Claims, 1 Drawing Sheet

FOREIGN PATENT DOCUMENTS

| WO | WO-01/27135 | 4/2001 |
|---|---|---|
| WO | WO-01/49279 | 7/2001 |
| WO | WO-02/30462 | 4/2002 |
| WO | WO-02/078703 | 10/2002 |
| WO | WO-02/078704 | 10/2002 |
| WO | WO02/078704 | 10/2002 |
| WO | WO03/088964 | 10/2003 |
| WO | WO-03/088964 | 10/2003 |
| WO | WO-2005/013800 | 2/2005 |
| WO | WO-2005/032343 | 4/2005 |
| WO | WO-2005/042700 | 5/2005 |
| WO | WO-2006/026430 | 3/2006 |
| WO | WO2006/026430 | 3/2006 |
| WO | WO-2007/123511 | 11/2007 |
| WO | 2008/011071 | 1/2008 |
| WO | WO-2008/083248 | 7/2008 |
| WO | WO-2008/083252 | 7/2008 |
| WO | WO-2008/089123 | 7/2008 |
| WO | 2008/109184 | 9/2008 |
| WO | 2008/109829 | 9/2008 |
| WO | 2009/126840 | 10/2009 |
| WO | 2010/000070 | 1/2010 |

OTHER PUBLICATIONS

Dierks, Christine et al., "Essential Role of Stromally induced hedgehog signaling in B-cell malignancies", Nature Medicine, (2007), pp. 1-8.

Dierks, Christine et al., "Expansion of Bcr-Abl-Positive Leukemic Stem Cells is Dependent on Hedgehog Pathway Activation", Cancer Cell, vol. 14, (2008), pp. 238-249.

Dormeyer, Wilma et al., "Plasma Membrane Proteomics of Human Embryonic Stem Cells and Human Embryonal Carcinoma Cells", Journal of Proteome Research, vol. 7, (2008), pp. 2936-2951.

Ehtesham, M. et al., "Ligand dependent activation of the hedgehog pathway in glioma progenitor cells", Ongogene (2007), pp. 1-10.

Feldmann, Georg et al., "Blockade of Hedgehog Signaling Inhibits Pancreatic Cancer Invasion and Metastases: A New Paradigm for Combination Therapy in Solid Cancers", Cancer Research, vol. 67, No. 5, (2007), pp. 2187-2196.

Geng, Ling et al., "Hedgehod signaling in the murine melanoma microenvironment", Angiogenesis, vol. 10, (2007) pp. 259-267.

Hegde, Ganapati V. et al., Hedgehog-Induced Survival of B-Cell Chronic Lymphocytic Leukemia Cells in a Stromal Cell Microenvironment: A Potential New Therapeutic Target, Mol. Cancer Res., vol. 6, (2008), pp. 1928-1936.

Ji, Zhenyu et al., "PKA, Not EPAC, Suppresses Hedgehog Activity and Regulates Glucocorticoid Sensitivity in Acute Lymphoblastic Leukemia Cells", Journal of Biological Chemistry, (2007), pp. 1-19.

Lindemann, Ralph K., "Stroma-Initiated Hedgehog Signaling Takes Center Stage in B-Cell Lymphoma", Cancer Research, vol. 68, No. 4, (2008), pp. 961-964.

Ma, Xiao-Li et al., "Study of Sonic Hedgehod signaling pathway related molecules in gastric carcinoma", World Journal of Gastroenterology, vol. 12, No. 25, (2006), pp. 3965-3969.

Manna, Joseph D. et al, "Metabolite Identification of IPI-609, a Novel and Potent Inhibitor of the Hedgehog Pathway, in Different Species", (2008), 1 page.

Masamune, T. et al., "Syntheses and NMR Spectra of 22,27-IMINO-17,23-Oxidojervane Derivatives", Tetrahedron, vol. 23, (1967), pp. 1591-1612).

Ohta, Miki et al., p53-Independent Negative Regulation of p21/Cyclin-Dependent Kinase-Interacting Protein 1 by the Sonic Hedgehog-Glioma-Associated Oncogene 1 Pathway in Gastric Carcinoma Cells, Cancer Research, vol. 65, No. 23, (2005), pp. 10822-10829.

Pasca Di Magliano, Marina et al., "Hedgehog Signalling in Cancer Formation and Maintenance", Nature Reviews/Cancer, vol. 3, (2003), pp. 903-911.

Rubin, Lee L. et al., "Targeting the Hedgehog Pathway in Cancer", Nature Reviews/Drug Discovery, vol. 5, (2006), pp. 1026-1033.

Saldanha, Gerald, "The Hedgehog signalling pathway and cancer", Journal of Pathology, vol. 193, (2001), pp. 427-432.

Shiotani, A. et al., "Sonic hedgehog and CDX2 expression in the stomach", J. Gastroenterol. Hepatol., (2008), S161-S166, (publication abstract only enclosed-1 page).

Sims-Mourtada, Jennifer et al., "Hedgehog: An Attribute to Tumor Regrowth after Chemoradiotherapy and a Target to Improve Radiation Response", Clinical Cancer Research, vol. 12, No. 21, (2006), pp. 6565-6572.

Stecca, Barbara et al., "Melanomas require HEDGEHOG-GLI signaling regulated by interactions between GLI1 and the RAS-MEK/AKT pathways", Proceedings of the National Academy of Sciences of the United States of America (PNAS), vol. 104, No. 14, (2007), pp. 5895-5900.

Steg, Adam et al., "Multiple Gene Expression Analyses in Paraffin-Embedded Tissues by TaqMan Low-Density Array", J. Molecular Diagnostics, vol. 8, (2006), pp. 76-83.

Taipale, Jussi et al., "Effects of oncogenic mutations in Smoothened and Patched can be reversed by cyclopamine", Nature, vol. 406, (2000), pp. 1005-1009.

Thievessen, I. et al., J. Cell Physiol., "Hedgehog signaling in normal urothelial cells and urothelial carcinoma cell lines", vol. 203, No. 2, (2005), pp. 372-377, (publication abstract only enclosed-1 page).

Travaglione, Veronica et al., "A novel Hh pathway inhibitor, IPI-926, delays recurrence post-chemotherapy in a primary human SCLC xenograft model #4611", Apr. 2008,1 page.

Tremblay, Martin R., "Semisynthetic Cyclopamine Analogues as Potent and Orally Bioavailable Hedgehog Pathway Antagonists", Journal of Medicinal Chemistry, vol. 51, (2008), pp. 6646-6649.

Wunder, Jay S. et al., "Opportunities for improving the therapeutic ratio for patients with sarcoma", Lancet Oncology, vol. 8, (2007), pp. 513-524.

Yang, Hai-Su and Hinds, Philip W., "pRb-mediated control of epithelial cell proliferation and Indian Hedgehog expression in mouse intestinal development", BMC Developmental Biology, vol. 7, No. 6, (2007), pp. 1-12.

Yoshizaki, Ayumi et al., "Expressionsl of sonic hedgehog, patched, smoothened and Gli-1 in human intestinal stromal tumors and their correlation with prognosis", World Journal of Gastroenterology, vol. 12, No. 35, (2006), pp. 5687-5691.

Zhao, Chen et al., Hedgehog signalling is essential for maintenance of cancer stem cells in myeloid leukaemia, Nature Letters, (Jan. 2009), pp. 1-5.

Chen, J.K. et al., "Inhibition of Hedgehog signaling by direct binding of cyclopamine to Smoothened", Genes and Development (2002) 16:2743-2748.

Qualtrough, D. et al. "Hedgehog signalling in colorectal tumour cells: induction of apoptosis with cyclopamine treatment" Int. J. Cancer (2004) 110(6): 831-837.

Extended European Search Report that was issued in connection with EP 08731680.8 (mail date of search report: Jul. 19, 2011), 4 pages.

Alexandre et al., "Transcriptional Activation of Hedgehog Target Genes in *Drosophila* is Mediated Directly by the Cubitus Interruptus Protein, a Member of the GLI Family of Zinc Finger DNA-Binding Proteins" Genes and Development (1996) 10:2003-2013.

Bale and Yu, "The Hedgehog Pathway and Basal Cell Carcinomas" Human Molecular Genetics (2001) 10:757-762.

Belloni et al., "Identification of Sonic Hedgehog as a Candidate Gene Responsible for Holosprosencephaly" Nature Genetics 1996 14:353-356.

Berge at al.,"Pharmaceutical Salts" Journal of Pharmaceutical Sciences (1977) 66:1-19.

Berman et al., "Widespread Requirement for Hedgehog Ligand Stimulation in Growth of Digestive Tract Tumours" Nature (2003) 425:846-851.

Berman et al., "Medulloblastoma Growth Inhibition by Hedgehog Pathway Blockade" Science (2002) 297:1559-1561.

Chen et al., "Inhibition of Hedgehog Signaling by Direct Binding of Cyclopamine to Smoothened" Genes and Development (2002)16:2743-2748.

Cooper et al., "Teratogen-Mediated Inhibition of Target Tissue Response to Shh Signaling" Science (1998) 280:1603-1607.

Fan et al., "Hedgehog Singallng Promotes Prostate Zenograft Tumor Growth" Endocrinology (2004) 145:3961-3970.

Karhadker at al., "Hedgehog Signalling in Prostate Regeneration, Neoplasia and Metastasis" Nature (2004) 431:707-712.
Kitajima et al., "Steroid Alkaloids of Fresh Bulbs of *Fritillaria thunbergll* Mlq. and of Crude Drug "BAI-MO" Prepared Therefrom" Heterocycles (1981) 15:791-796.
Kubo et al., "Hedgehog Signaling Pathway is a New Therapeutic Target for Patients with Breast Cancer" Cancer Research (2004) 64:6071-6074.
Lee at al., "Development of an Enzyme-linked Immunosorbent Assay for the Veratrum Plant Teratogens: Cyclopamine and Jervine" Journal of Agricultural and Food Chemistry (2003) 51:582.586.
Lewis and Veltmaat, "Next Stop, the Twilight Zone: Hedgehog Network Regulation of Mammary Gland Development" Journal of Mammary Gland Biology and Neoplasia (2004) 2:165-181.
Ma et al., "Frequent activation of the hedgehog pathway in advanced gastric adenocarcinomas" Carcinogenesis (2005) 10:1698-1705.
Mazur et al "Azasteroids III. 3-Aza-A-Homo Androgens" J. Org. Chem. (1953) 28:248-250.
Nakamura et al., "Induction of Osteogenic Differentiation by Hedgehog Proteins" Biochemical and Biophysical Research Communications (1997) 237:465-469.
Oka and Hara, "Regiospecific Beckmann Rearrangement of 3-Oxo-4-ene Steroid Oximes" J. Org. Chem. (1978) 43:3790-3791.
Oka and Hara, "Synthesis of A-Azasteroids by the Use of Specific Beckmann Rearrangement" Chemistry and Industry (1969) 168-170.
Patil et al., "Hedgehog Signaling in Human Hepatocellular Carcinoma" Cancer Biology & Therapy (2006) 5:111-117.
Peacock et al., "Hedgehog Signaling Maintains a Tumor Stem Cell Compartment in Multiple Myeloma" PNAS USA (2007) 104:4048-4053.
Pietsch et al., "Medulloblastomas of the Desmoplastic Variant Carry Mutations of the Human Homologue of *Drosophila* Patched" Cancer Research (1997) 57:2085-2088.
Quirk et al.,"The Smoothened Gene and Hedgehog Signal Transduction in *Drosophila* and Vertebrate Development" Cold Spring Harbor Symposium Quant. Biol. (1997) 62:217-226.
Rahman et al., "Alkaloids from *Veratrum album*" Phytochemistry (1991) 1:368-370.
Rasmusson et al., "Azasteroids: Structure-Activity Relationships for Inhibition of 5-alpha-Reductase and of Androgen Receptor Binding" J. Med. Chem. (1986) 2298-2315.
Reifenberger et al., "Missense Mutations in SMOH in Sporadic Basal Cell Carcinomas of the Skin and Primitive Neuroectodermal Tumors of the Central Nervous System" Cancer Research (1998) 58:1798-1803.
Sheng et al., "Activation of the Hedgehog Pathway in Advanced Prostate Cancer" Molecular Cancer (2004) 3:29-42.
Shroff and Harper, "3-Aza-A-Homoandrostenes" J. Med. Chem. (1969) 190-191.
Sicklick et al,, "Dysregulation of the Hedgehog Pathway in Human Hepatocarcinogenesis" Carcinogenesis (2006) 27:748-757.
TAS and AVCI, "Rapid Clearance of Psoriatic Skin Lesions Induced by Topical Cyclopamine" Dermatology (2004) 209:126-131.
Thayer et al., "Hedgehog is an Early and Late Mediator of Pancreatic Cancer Tumorigenesis" Nature (2003) 425:851-856.
Van Der Horst et al., "Hedgehog Stimulates Only Osteoblastic Differentiation of Undifferentiated KS483 cells" Bone (2003) 33:899-910.
Watkins et al.,"Hedgehog Signaling Within Airway Epithelial Progenitors and in Small-Cell Lung Cancer" Nature (2003) 422:313-317.
Williams et al., "Identification of a Small Molecule inhibitor of the Hedgehog Signaling Pathway: Effects on Basal Cell Carcinoma-Like Lesions" PNAS USA (2003) 100:4516-4621.
Xie et al., "Activating Smoothened Mutations in Sporadic Basal-Cell Carcinoma" Nature (1998) 391:90-92.
International Search Report for PCT/US05/30406, published as WO/2006/026430, mailed on Apr. 4, 2006, 2 pages.
Supplementary Partial European Search Report for EP 05791140.6, mailed Nov. 26, 2007, 4 pages.
International Search Report and Written Opinion for PCT/US2008/056229, mailed Aug. 11, 2008, 11 pages.
Qualtrough et al., Int. J, Cancer (2004) 110(6):831-837.

Brown, D. et al., "Structure-Activity Relation of Steroid Teratogens. 1. Jervine Ring System", J. Agric. Food Chem., vol. 26, No. 3, (1978), pp. 561-563.
Brown, D. et al,, "Structure-Activity Relation of Steroid Teratogens. 2. N-Substituted Jervines", J. Agric. Food Chem., vol. 26, No. 3, (1978), pp. 564-566.
Campbell, V. T. et al., "Direct Targeting of the Hedgehog Pathway in primary chondrosarcoma xenografts with Smoothened Inhibitor IPI-926", 2011 AACR Campbell LB380 Chonrosarcoma Poster, Infinity Pharmaceuticals, Inc.., Cambridge, MA, Hospital for Sick Children Toronto, Canada, Mount Sinai Hospital, Toronto, Canada, #LB380, 1 page.
Growdon, W. B. et al., "Hedgehog pathway inhibitor cyclopamine suppresses Glil expression and inhibits serous ovarian cancer xenograft growth", 40th Annual Meeting on Women's Cancer, Feb. 5-8, 2009, Henry B. Gonzalez Convention Center, San Antonio, TX, 16 pages.
Heretsch, P. et al., "Cyclopamine and Hedgehog Signaling: Chemistry, Biology, Medical Perspectives", Angew. Chem. Int. Ed., vol. 49, (2010), pp. 3418-3427.
Incardona, J. P. et al., "Cyclopamine Inhibition of Sonic Hedgehog Signal Transduction Is Not Mediated through Effects on Cholesterol Transport", Developmental Biology, vol. 224, (2000), pp. 440-452.
Lin, T. L. et al., "Self-Renewal of Acute Lymphocytic Leukemia Cells Is Limited by the Hedgehog Pathway Inhibitors Cyclopamine and IPI-926", PLoS One, vol. 5, Issue 12, e15262, (2010), 8 pages.
Olive, K. P. et al., "Inhibition of Hedgehog Signaling Enhances Delivery of Chemotherapy in a Mouse Model of Pancreatic Cancer", Science, vol. 324, (2009), pp. 1457-1461.
Pink, M. et al,, "Activity of IPI-926, a potent HH pathway inhibitor, in a novel model of medulloblastoma derived from Ptch/HIC +/− mice", 2008 AACR Infinity Pharmaceuticals, Inc. Medullo Oral Presentation, Cambridge, MA, Apr. 13, 2008, 15 pages.
Proctor, J. et al., "Hedgehog Signaling in Castration Resistant Prostate Cancer", AACR Annual Meeting, Apr. 17-21, 2010, Abstract #3857, Infinity Pharmaceuticals, Inc., Cambridge, MA, 14 pages.
Read, M. A., "Direct Targeting of Tumor Cells with Smoothed Inhibitor IPI-926", 2011 AACR Read IPI-926 Direct Targeting, Infinity Pharmaceuticals, Inc., Cambridge, MA, 27 pages.
Sawada, T. et al., "Asymmetric Catalysis of Intramolecular Cyclopropanation of 5-Aryl-1-diazo-1-mesitylsulfonyl-5-hexen-2-ones", Adv. Synth. Catal., vol. 347, (2005), pp. 1527-1532.
Tremblay, M. R. et al., "Development of Multi-kilogram Synthetic Route to IPI-926, a Novel Hedgehog Pathway Antagonistic for the Treatment of Malignant Diseases", Session Slides, Infinity Pharmaceuticals, Inc., Cambridge, MA, Apr. 2, 2011, 29 pages.
Tremblay, M.R. et al., Discovery of a Potent and Orally Active Hedgehog Pathway Antagonist (IPI-926), Journal of Medicinal Chemistry, (2009), pp. 4400-4418.
Tremblay, M. R. et al., "Recent patents for Hedgehog pathway inhibitors for the treatment of malignancy", Expert Opinion. Ther. Patents, 19(8), (2009), pp. 1039-1056.
Voituriez, A. et al., "Enantioselective Cyclopropanation with TADDOL-Derived Phosphate Ligands", Adv. Synth, Catal., vol. 348, (2006), pp. 2363-2370.
Extended European Search Report including the supplementary European Search Report and European Search Opinion that was issued in connection with EP 07870001.0 (mail date of search report: Dec. 2, 2010), 11 pages.
Extended European Search Report including the supplementary European Search Report and European Search Opinion that was issued in connection with EP 07870006.9 (mail date of search report: Dec. 2, 2010), 7 pages.
International Search Report and Written Opinion of the International Searching Authority for PCT/US07/88995, mailed on Aug. 1, 2008, 8 pages.
Extended European Search Report that was issued in connection with EP 10012778.6 (mail date of search report: Mar. 29, 2011), 7 pages.
Extended European Search Report that was issued in connection with EP 10012704,2 (mail date of search report: Mar. 29, 2011), 7 pages.
International Search Report and Written Opinion of the International Searching Authority for PCT/US2010/55879, mailed on Jan. 24, 2011, 12 pages.

Carter, B. et al., "Formulation for IPI-926 drug product, a novel oral Hedgehog pathway inhibitor in clinical development", AAPS Formulation for IPI-926 Poster, Infinity Pharmaceuticals, Inc., Cambridge, MA, 1 page. Nov. 2009.

Faia, K. et al., "Depilation Induced Anagen as a Model to Study Hedgehog Pathway Implications for Biomarker Development", Abstract #2827, Infinity Pharmaceuticals, Inc., Cambridge, MA, 1 page. Apr. 2008.

Grogan, M. J. et al., "Synthesis and Structure Activity Relationship of D-homo Cyclopamine Analogs: A-ring fused Heterocyclic Analogs", ACS MEDI 97 Poster, Infinity Pharmaceuticals, Inc., Cambridge, MA, 1 page. Mar. 2009.

Lescarbeau, A. et al., "Synthesis and Structure Activity Relationship of D-homo Cyclopamine Hedgehog Antagonists: 7-Membered A-ring Lactam Analogs", ACS MEDI 98 Poster, Infinity Pharmaceuticals, Inc., Cambridge, MA, 1 page. Mar. 2009.

Mandley, E. et al., "The Hh inhibitor IPI-926 delays tumor re-growth of a non-small cell lung cancer xenograft model following treatment with an EGFR targeted tyrosine kinase inhibitor", Infinity Pharmaceuticals, Inc., Cambridge, MA, #5045 Poster, 1 page. Apr. 2010.

Peacock, C.D. et al., "Visualization of Smoothened activation supports an essential role for Hedgehog signaling in the regulation of self-renewal in small cell lung cancer", Sidney Kimmel Comprehensive Cancer Center, Johns Hopkins University, Baltimore, MD, Monash Institute of Medical Research, Clayton, Australia, Infinity Pharmaceuticals, Inc., Cambridge, MA, 1 page. Apr. 2009.

Rudin, C. M. et al., "A Phase 1 Study of IPI-926, an Inhibitor of the Hedgehog Pathway, in Patients with Advanced or Metastatic Solid Tumors",Johns Hopkins University, Upper Aerodigestive Program, Baltimore, USA; Virginia G. Piper Cancer Center at Scottsdale Healthcare/TGen Clinical Research Services, Scottsdale, AZ; Stanford University School of Medicine, Department of Dermatology, Redwood City, CA; Yale University Cancer Center, Medical Oncology, New Haven, CT; McGill University, Lady Davis Institute and Segal Cancer Center, Montreal, Canada; Tom Baker Cancer Centre, Calgary, Canada; Infinity Pharmaceuticals, Inc., Cambridge, MA; University of Colorado School of Medicine, Medical Oncology, Aurora, CO, 1 page. Oct. 2010.

Travaglione, V. et al., "Activity of IPI-926, a novel inhibitor of the Hh pathway, in subcutaneous and orthotopically implanted xenograft tumors that express SHh ligand", Infinity Pharmaceuticals, Inc., Cambridge, MA, 1 page. Oct. 2008.

Travaglione, V. et al., "Induction of tumor-derived hedgehog ligand by chemotherapy", Ligand AACR poster, Infinity Pharmaceuticals, Inc., Cambridge, MA, Johns Hopkins University, Baltimore, MD and Monash Medical Center, Clayton, Australia, Abstract #323, 1 page. Apr. 2009.

Travaglione, V. et al., "The Hh inhibitor IPI-926 enhances tumor perfusion and nab-paclitaxel activity in a pancreatic xenograft model", Infinity Pharmaceuticals, Inc. Cambridge, MA, VisualSonics, Inc. Toronto, Ontario, Flagship Biosciences LLC, Abraxis Bioscience, LLC and Cambridge Research Institute, Cambridge, UK, 1 page. Apr. 2010.

Tremblay, M.R. et al., "Synthesis of novel, chemically stable D-homo-cyclopamine analogs via a cyclopropanation/ring-expansion sequence", GRC2007 IPI Hh Poster, Infinity Pharmaceuticals, Inc., Cambridge, MA, 1 page. Apr. 2007.

Tremblay, M. R. et al., "Synthesis and Structure Activity Relationship of D-homo Cyclopamine Analogs: 3-Substituted Analogs", ACS MEDI 99 Poster, Infinity Pharmaceuticals, Inc., Cambridge, MA, 1 page. Mar. 2009.

Villavicencio, E. et al., "Activity of the Hh pathway inhibitor IPI-926 in a mouse model of medulloblastoma", Fred Hutchinson Cancer Research Center, Seattle WA, Seattle Children's Hospital, Infinity Pharmaceuticals, Cambridge, MA, 1 page. Apr. 2009.

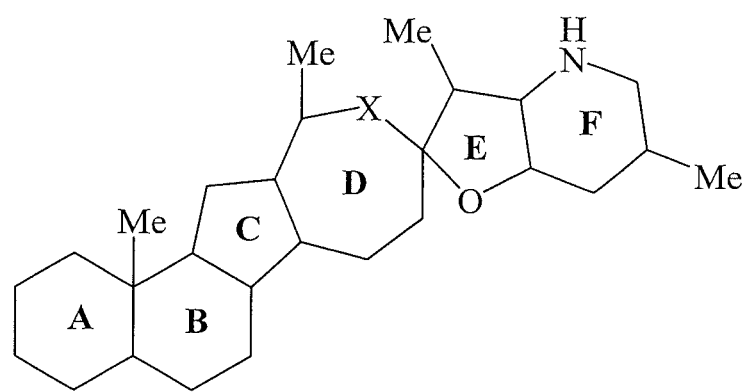
X = a bond or C(R)$_2$

CYCLOPAMINE LACTAM ANALOGS AND METHODS OF USE THEREOF

RELATED APPLICATIONS

This application is a continuation of U.S. application Ser. No. 13/102,395, filed May 6, 2011 now U.S. Pat. No. 8,293,760, which is a divisional of U.S. application Ser. No. 12/044,878, filed on Mar. 7, 2008 now U.S. Pat. No. 7,964,590, which claims the benefit of priority to U.S. Provisional Application Ser. No. 60/893,591, filed Mar. 7, 2007; each of these prior applications is incorporated herein by reference in its entirety.

TECHNICAL FIELD

The present invention generally relates to cyclopamine analogs, pharmaceutical compositions thereof, and methods for using such analogs and compositions. These compounds and compositions can be useful for the treatment of hedgehog mediated disorders, such as cancer and psoriasis.

BACKGROUND ART

The Hedgehog polypeptide is a secreted protein that functions as a signaling ligand in the hedgehog pathway. Three different forms of the hedgehog protein are found in humans; Sonic hedgehog (Shh), Desert hedgehog (Dhh) and Indian hedgehog (Ihh) Sonic hedgehog is the most prevalent hedgehog member in mammals and also is the best characterized ligand of the hedgehog family. Prior to secretion, Shh undergoes an intramolecular cleavage and lipid modification reaction. The lipid modified peptide is responsible for signaling activities.

Inhibition of the hedgehog pathway in certain cancers has been shown to result in inhibition of tumor growth. For example, anti-hedgehog antibodies have been shown to antagonize the function of the hedgehog pathway and inhibit the growth of tumors. Small molecule inhibition of hedgehog pathway activity has also been shown to result in cell death in a number of cancer types.

Research in this area has focused primarily on the elucidation of hedgehog pathway biology and the discovery of new hedgehog pathway inhibitors. Although inhibitors of the hedgehog pathway have been identified, there still exists the need to identify more potent inhibitors of the hedgehog pathway.

SUMMARY

The present invention relates to analogs of steroidal alkaloids, pharmaceutical compositions, and methods of using them.

The invention includes compounds of Formula 1, compositions comprising at least one such compound, and methods of using the compounds and compositions, where Formula 1 is:

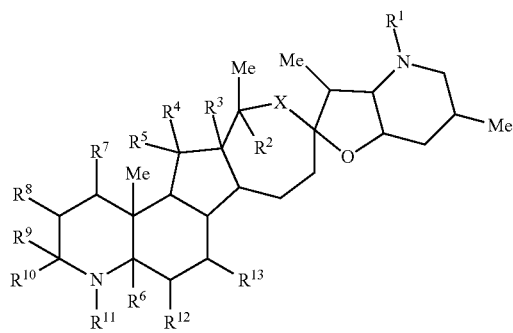

or a pharmaceutically acceptable salt thereof;
wherein;
$R^1$ is H, alkyl, alkenyl, alkynyl, aryl, cycloalkyl, hydroxyl, aralkyl, heteroaryl, heteroaralkyl, haloalkyl, alkoxyl, —$SR^{20}$, —$OR^{20}$, —$N(R^{20})(R^{20})$, —$C(O)R^{20}$, —$CO_2R^{20}$, —$OC(O)R^{20}$, —$C(O)N(R^{20})(R^{20})$, —$N(R^{20})C(O)R^{20}$, —$N(R^{20})C(O)(R^{20})(R^{20})$, —$S(O)R^{20}$, —$S(O)_2R^{20}$, —$S(O)_2N(R^{20})(R^{20})$, —$N(R^{20})S(O)_2R^{20}$, —$[(W)—C(O)]_pR^{20}$, —$[(W)—C(O)O]_pR^{20}$, —$[(W)—OC(O)]_pR^{20}$, —$[(W)—SO_2]_pR^{20}$, —$[(W)—N(R^{20})SO_2]_pR^{20}$, —$[(W)—C(O)N(R^{20})]_pR^{20}$, —$[(W)—O]_pR^{20}$, $[(W)—N(R^{20})]_pR^{20}$ or —$[(W)—S]_pR^{20}$;

each of $R^2$, $R^7$ and $R^{13}$ is independently H, alkyl, alkenyl, alkynyl, aryl, cycloalkyl, heterocycloalkyl, aralkyl, alkoxyl, aryloxy, acyloxy, halide, hydroxyl, amino, alkylamino, arylamino, acylamino, aralkylamino, alkylseleno, aralkylseleno, arylseleno, alkylthio, aralkylthio, arylthio, heteroaryl, or heteroaralkyl;

$R^3$ is H; or $R^2$ and $R^3$ taken together form a bond;

each of $R^4$ and $R^5$ independently is H, alkyl, alkenyl, alkynyl, aryl, cycloalkyl, nitrile, aralkyl, alkoxyl, aryloxy, acyloxy, halide, sulfhydryl, alkylthio, arylthio, aralkylthio, hydroxyl, amino, alkylamino, arylamino, acylamino, aralkylamino, heteroaryl, or heteroaralkyl;

or $R^4$ and $R^5$ taken together form =O, =S, =$N(R^{20})$, =N—$OR^{20}$ or =$N(N(R^{20})_2)$;

$R^6$ is H, alkyl, alkenyl, alkynyl, aryl, cycloalkyl, heterocycloalkyl, or aralkyl;

each of $R^8$ and $R^{12}$ independently is H, alkyl, alkenyl, alkynyl, aryl, cycloalkyl, heterocycloalkyl, or aralkyl; or $R^7$ and $R^8$ taken together form a bond; or $R^{12}$ and $R^{13}$ taken together form a bond each of $R^9$ and $R^{10}$ independently is H, alkyl, alkenyl, alkynyl, aryl, cycloalkyl, nitrile, aralkyl, heteroaryl, or heteroaralkyl; or $R^9$ and $R^{10}$ taken together form =O, =$N(R^{20})$, =N—$OR^{20}$, or =S;

$R^{11}$ is H, alkyl, alkenyl, alkynyl, aryl, cycloalkyl, heterocycloalkyl, aralkyl, —$C(O)R^{20}$, —$C(S)R^{20}$, —$CO_2R^{20}$, —$SO_2R^{20}$, —$C(O)N(R^{20})(R^{20})$, or —$C(S)N(R^{20})(R^{20})$; or has the formula —$[C(R^{20})_2]_q$—$R^{21}$;

$R^{20}$ independently for each occurrence is H, alkyl, alkenyl, alkynyl, aryl, cycloalkyl, heterocycloalkyl, aralkyl, heteroaryl, heteroaralkyl, or —$[C(R)_2]_q$—$R^{21}$, where each R is independently H or C1-C6 alkyl; or any two occurrences of $R^{20}$ can be taken together to form a 4-8 membered optionally substituted ring which contains 0-3 heteroatoms selected from N, O, S, and P;

$R^{21}$ independently for each occurrence is H, cycloalkyl, aryl, heteroaryl, heterocyclyl; alkoxyl, aryloxy, acyloxy, halide, sulfhydryl, alkylthio, arylthio, aralkylthio, hydroxyl, amino, acylamino, amido, or a carbonyl-containing group;

$R^{22}$ independently for each occurrence is H, halide, ester, amide, or nitrile;

p is 0, 1, 2, 3, 4, 5, or 6;

q is 0, 1, 2, 3, 4, 5, or 6;

W is a diradical;

X is a bond or —$C(R^{22})_2$— and each alkyl, alkenyl, alkynyl, aryl, cycloalkyl, heterocycloalkyl, aralkyl, heteroaryl, heteroaralkyl, whether alone or part of another group, is optionally substituted.

In other aspects, the invention includes a compound of formula 15, as well as compositions comprising at least one such compound and methods of using such compounds and compositions for treatment of conditions such as hyperproliferative disorders, including cancer, that are mediated by the hedgehog pathway. The compounds of formula 15 are represented by:

A compound of formula 15:

or a pharmaceutically acceptable salt thereof;
wherein;
each of A and B independently is —$N(R^{13})$—, —(C=O)—, or —(C=S)—;
$R^1$ is H, alkyl, alkenyl, alkynyl, aryl, cycloalkyl, hydroxyl, aralkyl, heteroaryl, heteroaralkyl, haloalkyl, alkoxyl, —$SR^{20}$, —$OR^{20}$, —$N(R^{20})(R^{20})$, —$C(O)R^{20}$, —$CO_2R^{20}$, —$OC(O)R^{20}$, —$C(O)N(R^{20})(R^{20})$, —$N(R^{20})C(O)R^{20}$, —$N(R^{20})C(O)N(R^{20})(R^{20})$, —$S(O)R^{20}$, —$S(O)_2R^{20}$, —$S(O)_2N(R^{20})(R^{20})$, —$N(R^{20})S(O)_2R^{20}$, —$[(W)—C(O)]_p R^{20}$, —$[(W)—C(O)O]_p R^{20}$, —$[(W)—OC(O)]_p R^{20}$, —$[(W)—SO_2]_p R^{20}$, —$[(W)—N(R^{20})SO_2]_p R^{20}$, —$[(W)—C(O)N(R^{20})]_p R^{20}$, $[(W)—O]_p R^{20}$, —$[(W)—N(R^{20})]_p R^{20}$, or —$[(W)—S]_p R^{20}$;
each of $R^2$, $R^7$ and $R^{10}$ is independently H, alkyl, alkenyl, alkynyl, aryl, cycloalkyl, heterocycloalkyl, aralkyl, alkoxyl, aryloxy, acyloxy, halide, hydroxyl, amino, alkylamino, arylamino, acylamino, aralkylamino, alkylseleno, aralkylseleno, arylseleno, alkylthio, aralkylthio, arylthio, heteroaryl, or heteroaralkyl;
$R^3$ is H; or $R^2$ and $R^3$ taken together form a bond;
each of $R^4$ and $R^5$ independently is H, alkyl, alkenyl, alkynyl, aryl, cycloalkyl, nitrile, aralkyl, alkoxyl, aryloxy, acyloxy, halide, sulfhydryl, alkylthio, arylthio, aralkylthio, hydroxyl, amino, alkylamino, arylamino, acylamino, aralkylamino, heteroaryl, or heteroaralkyl; or $R^4$ and $R^5$ taken together form =O, =S, =$N(R^{20})$, =N—$OR^{20}$ or =$N(N(R^{20})_2)$;
$R^6$ is H, alkyl, alkenyl, alkynyl, aryl, cycloalkyl, heterocycloalkyl, or aralkyl; or $R^6$ and $R^{10}$ taken together form a bond;
each of $R^{11}$, $R^{12}$, $R^{14}$ and $R^{15}$ a independently is H, alkyl, alkenyl, alkynyl, aryl, cycloalkyl, heterocycloalkyl, or aralkyl; or $R^{11}$ and $R^{12}$ taken together form a bond; or $R^7$ and $R^{14}$ taken together form a bond;

$R^{13}$ is H, alkyl, alkenyl, alkynyl, aryl, cycloalkyl, heterocycloalkyl, aralkyl, —$C(O)R^{20}$, —$C(S)R^{20}$, $CO_2R^{20}$, —$SO_2R^{20}$, —$C(O)N(R^{20})(R^{20})$, or has the formula —$C(S)N(R^{20})(R^{20})$; or has the formula —$[C(R^{20})_2]—R^{21}$;

$R^{20}$ independently for each occurrence is H, alkyl, alkenyl, alkynyl, aryl, cycloalkyl, heterocycloalkyl, aralkyl, heteroaryl, heteroaralkyl, or —$[C(R)_2]_q—R^{21}$, where each R is independently H or C1-C6 alkyl; or any two occurrences of $R^{20}$ can be taken together to form a 4-8 membered optionally substituted ring which contains 0-3 heteroatoms selected from N, O, S, and P;

$R^{21}$ independently for each occurrence is H, cycloalkyl, aryl, heteroaryl, heterocyclyl; alkoxyl, aryloxy, acyloxy, halide, sulfhydryl, alkylthio, arylthio, aralkylthio, hydroxyl, amino, acylamino, amido, or a carbonyl-containing group;

$R^{22}$ independently for each occurrence is H, halide, ester, amide, or nitrile;

p is 0, 1, 2, 3, 4, 5, or 6;

q is 0, 1, 2, 3, 4, 5, or 6;

W is a diradical;

X is a bond or —$C(R^{22})_2$—;

and each alkyl, alkenyl, alkynyl, aryl, cycloalkyl, heterocycloalkyl, aralkyl, heteroaryl, heteroaralkyl, whether alone or part of another group, is optionally substituted; provided that when A is —$N(R^{13})$—; B must be —(C=O)—, or —(C=S)—; and provided that when A is —(C=O)—, or —(C=S)—; B must be —$N(R^{13})$—.

BRIEF DESCRIPTION OF THE DRAWINGS

FIG. 1 depicts the carboskeleton of a steroidal alkaloid with the rings labeled A-F.

MODES OF CARRYING OUT THE INVENTION

Definitions

The definitions of terms used herein are meant to incorporate the present state-of-the-art definitions recognized for each term in the chemical and pharmaceutical fields. Where appropriate, exemplification is provided. The definitions apply to the terms as they are used throughout this specification, unless otherwise limited in specific instances, either individually or as part of a larger group.

As used herein, the definition of each expression, e.g., alkyl, m, n, etc., when it occurs more than once in any structure, is intended to be independent of its definition elsewhere in the same structure.

The term "acyl" as used herein refers to a group of the general formula R—C(=O)—, where R can be H, alkyl, aryl, or aralkyl. In typical acyl groups, R is H or C1-C6 alkyl, which is optionally substituted, or R can be aralkyl, wherein the aryl portion of the aralkyl is a 5-7 membered aromatic or heteroaromatic ring, and the alkyl portion is a C1-C4 alkylene group; and both the alkyl and aryl portions are optionally substituted as described herein for such groups. Benzyl, p-methoxybenzyl, and phenylethyl are examples of a typical aralkyl.

The term "acylamino" refers to a moiety that may be represented by the general formula:

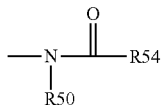

wherein R50 is as defined below, and R54 represents a hydrogen, an alkyl, an alkenyl or —(CH$_2$)$_m$—R61, where m and R61 are as defined below.

The terms "alkenyl" and "alkynyl" refer to unsaturated aliphatic groups analogous in length and possible substitution to the alkyls described below, but that contain at least one double or triple bond respectively. Alkenyl and alkynyl groups may be substituted with the same groups that are suitable as substituents on alkyl groups, to the extent permitted by the available valences. Typical alkenyl and alkynyl groups contain 2-10 carbons in the backbone structure.

The terms "alkoxyl" or "alkoxy" refers to an alkyl group, as defined below, having an oxygen radical attached thereto. Representative alkoxyl groups include methoxy, ethoxy, propyloxy, tert-butoxy and the like. The alkyl portion of an alkoxy group is sized like the alkyl groups, and can be substituted by the same groups that are suitable as substituents on alkyl groups, to the extent permitted by the available valences.

The term "alkyl" refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. In certain embodiments, a straight chain or branched chain alkyl has 30 or fewer carbon atoms in its backbone (e.g., $C_1$-$C_{30}$ for straight chain, $C_3$-$C_{30}$ for branched chain), 20 or fewer. Typically, an alkyl group contains 1-10 carbon atoms as its backbone, and may be substituted or unsubstituted. Likewise, certain cycloalkyls have from 3-10 carbon atoms in their ring structure, and others have 5, 6 or 7 carbons in the ring structure. Unless otherwise indicated, alkyl and cycloalkyl groups, whether alone or as part of another group such as an aralkyl group, can be substituted by suitable substituents such as, but not limited to, halogen, azide, oxo, acyl, cycloalkyl, hydroxyl, alkoxyl, amino, nitro, sulfhydryl, imino, oximino, amido, acylamino, phosphonate, phosphinate, carbonyl, carboxylic acids or their esters or amides, silyl, alkoxy, alkylthio, alkylsulfonyl, alkylsulfonamido, ketone, aldehyde, ester, heterocyclyl, aromatic or heteroaromatic moieties, —CF$_3$, —CN, and the like.

Where alkyl, alkenyl, or alkynyl is part of another group, such as in alkoxy, alkylthio, etc., or it is a substituent on another group, it is frequently an optionally substituted lower alkyl group or lower alkenyl group, or lower alkynyl group having up to six carbon atoms. For such purposes, the typical substituents include halo, —OR', —SR', —SO$_2$R', —SO$_2$NR'$_2$, COOR', CONR'$_2$, oxo, —NR'$_2$, NR'C(O)R', NR'C(O)OR', NR'SO$_2$R', OC(O)R', where each R' is independently H or unsubstituted $C_1$-$C_6$ alkyl, $C_2$-$C_6$ alkenyl, or $C_2$-$C_6$ alkynyl.

The term "alkylthio" refers to an alkyl group, as defined above, having a sulfur radical attached thereto. In certain embodiments, the "alkylthio" moiety is represented by one of —S-alkyl, —S-alkenyl, —S-alkynyl, and —S—(CH$_2$)$_m$—R61, wherein m and R61 are defined below. Representative alkylthio groups include methylthio, ethyl thio, and the like.

The term "amido" is art recognized as an amino-substituted carbonyl and includes a moiety that may be represented by the general formula:

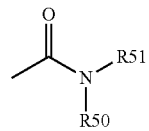

wherein R50 and R51 are as defined below. Certain embodiments of the amide in the present invention will not include imides which may be unstable.

The terms "amine" and "amino" are art-recognized and refer to both unsubstituted and substituted amines, e.g., a moiety that may be represented by the general formulas:

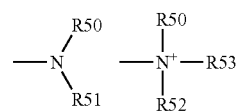

wherein R50, R51 and R52 and R53 each independently represent a hydrogen, an alkyl, an alkenyl, —(CH$_2$)$_m$—R61, or R50 and R51 (or R50 and R52 in the ammonium species), taken together with the N atom to which they are attached complete a heterocycle having from 4 to 8 atoms in the ring structure; R61 represents an aryl, a cycloalkyl, a cycloalkenyl, a heterocycle or a polycycle; and m is zero or an integer in the range of 1 to 8. In other embodiments, R50 and R51 (and optionally R52) each independently represent a hydrogen, an alkyl, an alkenyl, or —(CH$_2$)$_m$—R61. Thus, the term "alkylamine" includes an amine group, as defined above, having a substituted or unsubstituted alkyl attached thereto, i.e., at least one of R50 and R51 is an alkyl group.

The term "aralkyl", as used herein, whether alone or as part of a group name such as, for example, aralkyloxy, refers to an alkyl group as described herein substituted with an aryl group as described herein (e.g., an aromatic or heteroaromatic group). Both the alkyl and the aryl portion of each aralkyl group are typically optionally substituted. Typical aralkyl groups include, for example, groups of general formula Ar—(CH$_2$)$_t$—, where Ar represents an aryl ring and t is an integer from 1-6.

The term "aryl" as used herein, whether alone or as part of another name such as 'aryloxy', includes 5-, 6- and 7-membered single-ring aromatic groups that may include from zero to four heteroatoms selected from N, O and S as ring members, as well as fused bicyclic an tricyclic systems consisting of such rings, for example, benzene, anthracene, naphthalene, pyrene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics." The aromatic ring may be substituted as available valences permit at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carbonyl-containing group, silyl, ether, alkylthio, sulfonyl, sulfonamido, ketone, aldehyde, ester, heterocyclyl, aromatic or heteroaromatic moieties, —CF$_3$, —CN, or the like. The term "aryl" also includes polycyclic ring systems having two or more cyclic rings, often two or three rings, in which two or more carbons are common to two adjoining rings (the rings are "fused rings") wherein at least one of the rings is aromatic, e.g., the other cyclic rings may be cycloalkyls, cycloalkenyls, cycloalkynyls, aryls and/or heterocyclyls. In some embodiments, each aryl is selected from phenyl, thiophene, furan, pyrrole, pyridine, pyrimidine, pyrazole, imidazole, oxazole, thiazole, isoxazole and isothiazole. Phenyl is sometimes preferred.

The term "Brønsted acid" refers to any substance that can act as a hydrogen ion (proton) donor.

The term "carbonyl-containing group" includes such moieties as may be represented by the general formulas:

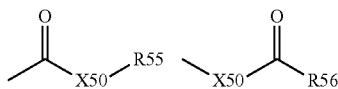

wherein X50 is a bond or represents an oxygen or a sulfur, and each of R55 and R56 represents independently a hydrogen, an alkyl, an alkenyl, —(CH$_2$)$_m$—R61 or a cation representing a pharmaceutically acceptable salt, where m and R61 are defined above. In some embodiments where a carbonyl-containing group is present, it is a carboxylic acid or ester, or an acyloxy group; X50 is O in such embodiments, and R55 or R56, whichever is present, is often H or an optionally substituted alkyl group.

The term "diradical" refers to any of a series of divalent groups from alkyl, alkenyl, alkynyl, aryl, cycloalkyl, heterocycloalkyl, aralkyl, heteroaryl, and heteroaralkyl groups, each of which can be optionally substituted. For example,

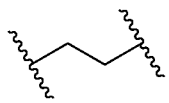 [SMILES: *CC*]

is an alkyl diradical;

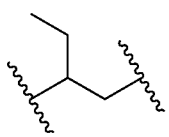 [SMILES: *CC(*)CC]

is also an alkyl diradical;

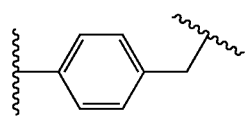 [SMILES: *Cc1ccc(*)cc1]

is an aralkyl diradical; and

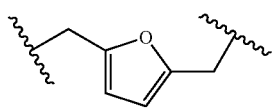 [SMILES: *Cc1ccc(C*)o1]

is an (alkyl)heteroaralkyl diradical. Typical examples include alkylenes of general structure (CH$_2$)$_x$ where x is 1-6, and corresponding alkenylene and alkynylene linkers having 2-6 carbon atoms and containing one or more double or triple bonds; cycloalkylene groups having 3-8 ring members; groups such as (CH$_2$)$_a$C(=O)(CH$_2$)$_b$, where a and b are each integers from 0-4; and aralkyl groups wherein one open valence is on the aryl ring and one is on the alkyl portion such as

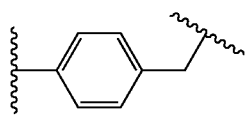 [SMILES: *Cc1ccc(*)cc1]

and its isomers. The alkyl, alkenyl, alkynyl, aryl, cycloalkyl, heterocycloalkyl, aralkyl, heteroaryl, and heteroaralkyl portions of a diradical are optionally substituted as described above.

The term "haloalkyl", as used herein, refers to an alkyl group where anywhere from 1 to all hydrogens have been replaced with a halide. A "perhaloalkyl" is where all of the hydrogens have been replaced with a halide.

The term "heteroatom" as used herein means an atom of any element other than carbon or hydrogen. Examples of heteroatoms include boron, nitrogen, oxygen, phosphorus, sulfur and selenium. Typically, the heteroatoms are selected from N, O and S.

The term 'heteroalkyl' and 'heterocycloalkyl' refer to alkyl and cycloalkyl groups as described herein, wherein at least one carbon atom of the alkyl or cycloalkyl portion is replaced by a heteroatom selected from N, O and S. Typical examples include methoxymethyl, allylthioethyl, dimethylaminoethyl, and tetrahydrofuranyl.

The terms "heterocyclyl" or "heterocyclic group" refer to 3- to 10-membered ring structures, in some instances from 3- to 7-membered rings, whose ring structures include at least one carbon atom and one to four heteroatoms. Heterocycles can also be polycycles. Heterocyclyl groups include, for example, thiophene, thianthrene, furan, pyran, isobenzofuran, chromene, xanthene, phenoxathiin, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring may be substituted at one or more positions with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carbonyl-containing group, silyl, ether, alkylthio, sulfonyl, ketone, aldehyde, ester, a heterocyclyl, an aromatic or heteroaromatic moiety, —CF$_3$, —CN, or the like.

The term "Lewis acid" refers to any substance that can act as an electron pair acceptor.

Unless the number of carbons is otherwise specified, "lower alkyl" as used herein means an alkyl group, as defined above, but having from one to ten carbons, in some embodiments from one to six carbon atoms in its backbone structure. Likewise, "lower alkenyl" and "lower alkynyl" have similar chain lengths. Certain alkyl groups are lower alkyls. In some embodiments, a substituent designated herein as alkyl is a lower alkyl.

As used herein, the term "nitro" means —$NO_2$; the term "halogen" designates —F, —Cl, —Br or —I; the term "sulfhydryl" means —SH; the term "hydroxyl" means —OH; and the term "sulfonyl" means —$SO_2$—.

The term "optionally substituted" as used herein indicates that a specified group may be unsubstituted or it may be substituted with one or more substituents to the extent consistent with the number of available valences on the specified group. In some embodiments, each optionally substituted group is substituted with up to four substituents or with 0-3 substituents.

The term "oxo" refers to a carbonyl oxygen

The terms "polycyclyl" or "polycyclic group" refer to two or more rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle may be substituted with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carbonyl-containing group, silyl, ether, alkylthio, sulfonyl, ketone, aldehyde, ester, a heterocyclyl, an aromatic or heteroaromatic moiety, —$CF_3$, —CN, or the like.

The phrase "protecting group" as used herein means temporary substituents which protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P. G. M., *Protective Groups in Organic Synthesis*, 2$^{nd}$ ed.; Wiley: New York, 1991).

The term "sugar" as used herein refers to a natural or an unnatural monosaccharide, disaccharide or oligosaccharide comprising one or more pyranose and/or furanose rings. The sugar may be covalently bonded to the steroidal alkaloid of the present invention through an ether linkage or through an alkyl linkage. In certain embodiments the saccharide moiety may be covalently bonded to a steroidal alkaloid of the present invention at an anomeric center of a saccharide ring. Sugars may include, but are not limited to ribose, arabinose, xylose, lyxose, allose, altrose, glucose, mannose, gulose, idose, galactose, talose, glucose, and trehalose.

The terms "triflyl", "tosyl", "mesyl", and "nonaflyl" refer to trifluoromethanesulfonyl, p-toluenesulfonyl, methanesulfonyl, and nonafluorobutanesulfonyl groups, respectively. The terms "triflate", "tosylate", "mesylate", and "nonaflate" refer to trifluoromethanesulfonate ester, p-toluenesulfonate ester, methanesulfonate ester, and nonafluorobutanesulfonate ester functional groups and molecules that contain said groups, respectively.

The term "thioxo" refers to a carbonyl sulfur (═S).

The abbreviations Me, Et, Ph, Tf, Nf, Ts, Ms represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the *Journal of Organic Chemistry*; this list is typically presented in a table entitled *Standard List of Abbreviations*.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc.

Where two groups are "taken together form a bond," if the groups are attached to atoms that are not otherwise directly bonded to each other, they represent a bond between the atoms to which they are attached. If the groups are on atoms that are directly bonded to each other, they represent an additional bond between those two atoms. Thus, for example, when $R^2$ and $R^3$ taken together form a bond, the structure —C(A)$R^2$—C(B)$R^3$— represents —C(A)═C(B)—.

The invention, in one aspect, includes compounds of Formula 1:

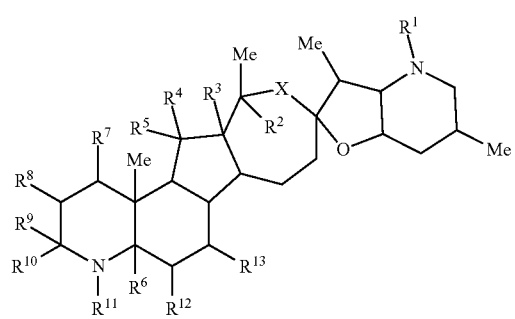

and the pharmaceutically acceptable salt thereof, wherein:
$R^1$ is H, alkyl, alkenyl, alkynyl, aryl, cycloalkyl, hydroxyl, aralkyl, heteroaryl, heteroaralkyl, haloalkyl, alkoxyl, —$SR^{20}$, —$OR^{20}$, —$N(R^{20})(R^{20})$, —$C(O)R^{20}$, —$CO_2R^{20}$, —$OC(O)R^{20}$, —$C(O)N(R^{20})(R^{20})$, —$N(R^{20})C(O)R^{20}$, —$N(R^{20})C(O)N(R^{20})(R^{20})$, —$S(O)R^{20}$, —$S(O)_2R^{20}$, —$S(O)_2N(R^{20})(R^{20})$, —$N(R^{20})S(O)_2R^{20}$, —[(W)—C(O)]$_p$$R^{20}$, —[(W)—C(O)O]$_p$$R^{20}$, —[(W)—OC(O)]$_p$$R^{20}$, —[(W)—$SO_2$]$_p$$R^{20}$, —[(W)—N($R^{20}$)$SO_2$]$_p$$R^{20}$, —[(W)—C(O)N($R^{20}$)]$_p$$R^{20}$, —[(W)—O]$_p$$R^{20}$, —[(W)—N($R^{20}$)]$_p$$R^{20}$, or —[(W)—S]$_p$$R^{20}$;
each of $R^2$, $R^7$ and $R^{13}$ is independently H, alkyl, alkenyl, alkynyl, aryl, cycloalkyl, heterocycloalkyl, aralkyl, alkoxyl, aryloxy, acyloxy, halide, hydroxyl, amino, alkylamino, arylamino, acylamino, aralkylamino, alkylseleno, aralkylseleno, arylseleno, alkylthio, aralkylthio, arylthio, heteroaryl, or heteroaralkyl;
$R^3$ is H; or $R^2$ and $R^3$ taken together form a bond;
each of $R^4$ and $R^5$ independently is H, alkyl, alkenyl, alkynyl, aryl, cycloalkyl, nitrile, aralkyl, alkoxyl, aryloxy, acyloxy, halide, sulfhydryl, alkylthio, arylthio, aralkylthio, hydroxyl, amino, alkylamino, arylamino, acylamino, aralkylamino, heteroaryl, or heteroaralkyl; or $R^4$ and $R^5$ taken together form ═O, ═S, ═N($R^{20}$), ═N—$OR^{20}$ or ═N(N($R^{20}$)$_2$);
$R^6$ is H, alkyl, alkenyl, alkynyl, aryl, cycloalkyl, heterocycloalkyl, or aralkyl;
each of $R^8$ and $R^{12}$ independently is H, alkyl, alkenyl, alkynyl, aryl, cycloalkyl, heterocycloalkyl, or aralkyl; or $R^7$ and $R^8$ taken together form a bond; or $R^{12}$ and $R^{13}$ taken together form a bond
each of $R^9$ and $R^{10}$ independently is H, alkyl, alkenyl, alkynyl, aryl, cycloalkyl, nitrile, aralkyl, heteroaryl, or heteroaralkyl; or $R^9$ and $R^{10}$ taken together form ═O, ═N($R^{20}$), ═N—$OR^{20}$, or ═S;
$R^{11}$ is H, alkyl, alkenyl, alkynyl, aryl, cycloalkyl, heterocycloalkyl, aralkyl, —$C(O)R^{20}$, —$C(S)R^{20}$, —$CO_2R^{20}$, —SO$_2$R$^{20}$, —C(O)N(R$^{20}$)(R$^{20}$), or —C(S)N(R$^{20}$)(R$^{20}$); or has the formula —[C(R$^{20}$)$_2$]$_q$—R$^{21}$;

R$^{20}$ independently for each occurrence is H, alkyl, alkenyl, alkynyl, aryl, cycloalkyl, heterocycloalkyl, aralkyl, heteroaryl, heteroaralkyl, or —[C(R)$_2$]$_q$—R$^{21}$, where each R is independently H or C1-C6 alkyl; or any two occurrences of R$^{20}$ can be taken together to form a 4-8 membered optionally substituted ring which contains 0-3 heteroatoms selected from N, O, S, and P;

R$^{21}$ independently for each occurrence is H, cycloalkyl, aryl, heteroaryl, heterocyclyl; alkoxyl, aryloxy, acyloxy, halide, sulfhydryl, alkylthio, arylthio, aralkylthio, hydroxyl, amino, acylamino, amido, or carbonyl-containing group;

R$^{22}$ independently for each occurrence is H, halide, ester, amide, or nitrile;

p is 0, 1, 2, 3, 4, 5, or 6;

q is 0, 1, 2, 3, 4, 5, or 6;

W is a diradical; and

X is a bond or —C(R$^{22}$)$_2$—;

and each alkyl, alkenyl, alkynyl, aryl, cycloalkyl, heterocycloalkyl, aralkyl, heteroaryl, heteroaralkyl, whether alone or part of another group, is optionally substituted.

Certain compounds of the present invention may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention. Where tautomers are possible in a compound of the invention, the invention includes each tautomeric form. Where stereochemistry of a chiral center is not expressly depicted or described, the structure includes each isomer at that center. Where the absolute stereochemistry of a compound is depicted in a drawing of a structure, the depicted isomer is a preferred embodiment; a racemic mixture of each specifically depicted compound is also an embodiment of the invention.

In some embodiments, the invention provides a compound of formula 1, wherein each of R$^7$, R$^8$, R$^{12}$ and R$^{13}$ represents H. In some embodiments, R$^{11}$ is H or optionally substituted C1-C6 alkyl.

In some of the foregoing embodiments of the compounds of formula 1, R$^4$ and R$^5$ are both H; or R$^4$ and R$^5$ taken together form =O.

In some of the foregoing embodiments, R$^2$ and R$^3$ taken together form a bond, so the D-ring contains a double bond. In such embodiments, X is sometimes a bond and it is sometimes CH$_2$. In some embodiments, R$^2$ and R$^3$ are each H.

In some of the foregoing embodiments, R$^9$ and R$^{10}$ are each H; in others, R$^9$ and R$^{10}$ taken together form =O or =S, so that the A-ring is a lactam or thiolactam. In some embodiments, R$^6$ is H or Me.

In some of the foregoing embodiments, R$^1$ is preferably H or an optionally substituted C1-C6 alkyl or aryl-(C1-C6)-alkyl. In other of the foregoing embodiments, R$^1$ is preferably of the form C(O)R$^{20}$, SO$_2$R$^{20}$ or CO$_2$R$^{20}$, where R$^{20}$ is an optionally substituted C1-C6 alkyl or aryl-(C1-C6)-alkyl. In certain embodiments, when R$^1$ is COOR$^{20}$, R$^{20}$ is benzyl, methyl, ethyl, or tert-butyl.

In some of the foregoing embodiments, R$^{11}$ is preferably H or an optionally substituted C1-C6 alkyl or aryl-(C1-C6)-alkyl. In other of the foregoing embodiments, R$^{11}$ is preferably of the form C(O)R$^{20}$, SO$_2$R$^{20}$ or CO$_2$R$^{20}$, where R$^{20}$ is an optionally substituted C1-C6 alkyl or aryl-(C1-C6)-alkyl. In certain embodiments, when R$^1$ is COOR$^{20}$, R$^{20}$ is benzyl, methyl, ethyl, or tert-butyl.

In some of the foregoing embodiments, R$^7$ and R$^8$ are both H; in other embodiments, when R$^7$ and R$^8$ are not H, R$^7$ and R$^8$ taken together form a bond, so the A-ring contains a double bond.

In some of the foregoing embodiments, p is 0 or 1 independently at each occurrence. In some such embodiments, p is 1.

In some embodiments, the compound of Formula 1 is a compound of formula 9:

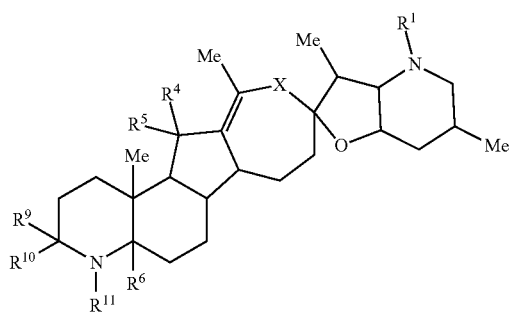

or a pharmaceutically acceptable salt thereof;
wherein;
R$^1$, R$^4$, R$^5$, and R$^6$ are as defined above for formula 1,
each of R$^9$ and R$^{10}$ independently is H, alkyl, alkenyl, alkynyl, aryl, cycloalkyl, nitrile, aralkyl, heteroaryl, or heteroaralkyl; or R$^9$ and R$^{10}$ taken together form =O, =N(R$^{20}$), =N—OR$^{20}$, or =S;

R$^{11}$ is H, alkyl, alkenyl, alkynyl, aryl, cycloalkyl, heterocloalkyl, aralkyl, —C(O)R$^{20}$, —C(S)R$^{20}$, —CO$_2$R$^{20}$, —SO$_2$R$^{20}$, —C(O)N(R$^{20}$)(R$^{20}$), or —C(S)N(R$^{20}$)(R$^{20}$); or has the formula —[C(R$^{20}$)$_2$]$_q$—R$^{21}$;

R$^{20}$ independently for each occurrence is H, alkyl, alkenyl, alkynyl, aryl, cycloalkyl, heterocycloalkyl, aralkyl, heteroaryl, heteroaralkyl, or —[C(R)$_2$]$_q$—R$^{21}$, where each R is independently H or C1-C6 alkyl; or any two occurrences of R$^{20}$ can be taken together to form a 4-8 membered optionally substituted ring which contains 0-3 heteroatoms selected from N, O, S, and P;

R$^{21}$ independently for each occurrence is H, cycloalkyl, aryl, heteroaryl, heterocyclyl; alkoxyl, aryloxy, acyloxy, halide, sulfhydryl, alkylthio, arylthio, aralkylthio, hydroxyl, amino, acylamino, amido, or carbonyl-containing group; and p is 0, 1, 2, 3, 4, 5, or 6;

q is 0, 1, 2, 3, 4, 5, or 6;

W is a diradical;

X is a bond or —CH$_2$—;

and each alkyl, alkenyl, alkynyl, aryl, cycloalkyl, heterocycloalkyl, aralkyl, heteroaryl, heteroaralkyl, whether alone or part of another group, is optionally substituted.

In some embodiments of the compound of formula 9, X is —CH$_2$—. In other embodiments, X is a bond.

In some of the foregoing embodiments of compounds of formula 9, R$^6$ is H or optionally substituted C1-C6 alkyl. Sometimes R$^6$ is Me.

In some embodiments of the compounds of formula 9, R$^1$ is H. In other embodiments, R$^1$ is alkyl, alkenyl, alkynyl, aryl, cycloalkyl, hydroxyl, aralkyl, heteroaryl, heteroaralkyl, haloalkyl, alkoxyl, —C(O)N(R$^{20}$)(R$^{20}$), COOR$^{20}$, —[C(R$^{20}$)$_2$]$_p$—R$^{20}$, —[(W)—N(R$^{20}$)C(O)]$_p$R$^{20}$, —[(W)—C $(O)]_pR^{20}$, —[(W)—C(O)O]$_p$R$^{20}$, —[(W)—OC(O)]$_p$R$^{20}$, —[(W)—SO$_2$]$_p$R$^{20}$, —[(W)—N(R$^{20}$)SO$_2$]$_p$R$^{20}$, —[(W)—C(O)N(R$^{20}$)]$_p$R$^{20}$, —[(W)—O]$_p$R$^{20}$, —[(W)—N(R$^{20}$)]$_p$R$^{20}$, or —[(W)—S]$_p$R$^{20}$. Often R$^1$ is H, optionally substituted C1-C6 alkyl, C(O)R$^{20}$, SO$_2$R$^{20}$, or it is COOR$^{20}$. In certain embodiments, R$^1$ is H or C(O)R$^{20}$ or COOR$^{20}$, where R$^{20}$ is benzyl, methyl, ethyl, or tert-butyl. In some of the foregoing embodiments, p is 0 or 1 independently at each occurrence. In some such embodiments, p is 1.

In some embodiments of the compounds of formula 9, R$^4$ and R$^5$ are both H. In other such embodiments, R$^4$ and R$^5$ taken together form a bond.

In some embodiments of the compounds of formula 9, R$^9$ and R$^{10}$ taken together form =O or =S. In many such embodiments, they are taken together to form =O.

In some embodiments, the compounds of formula 9 is selected from:

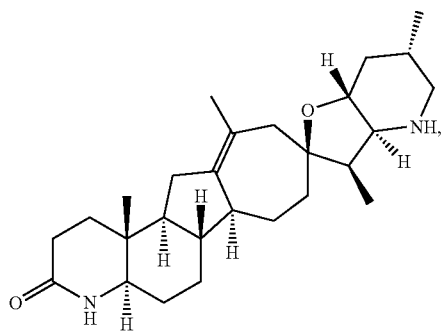

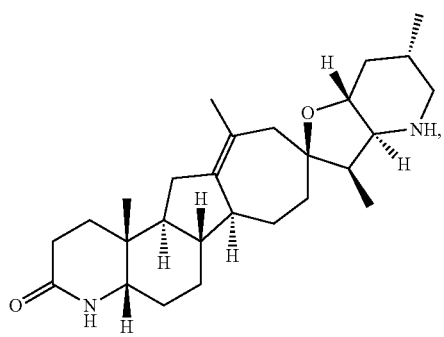

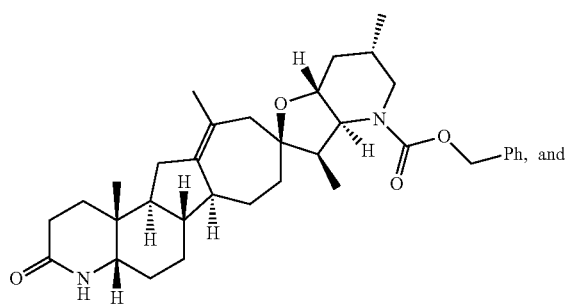

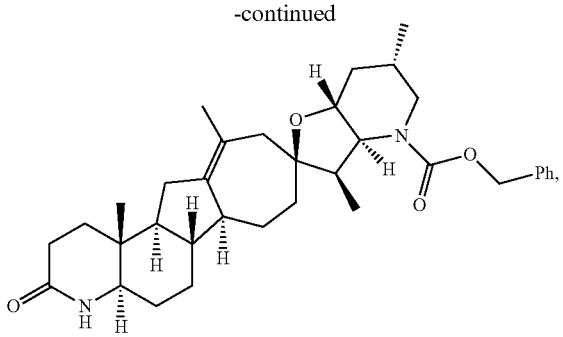

and the pharmaceutically acceptable salts of these compounds.

In another aspect, the invention provides a compound of formula 15:

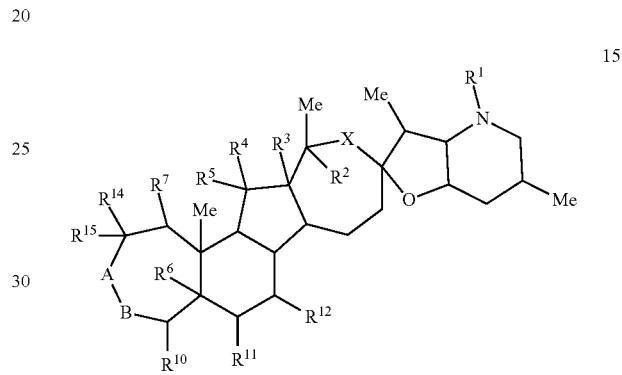

or a pharmaceutically acceptable salt thereof, wherein;
each of A and B independently is —N(R$^{13}$)—, —(C=O)—, or —(C=S)—;
R$^1$ is H, alkyl, alkenyl, alkynyl, aryl, cycloalkyl, hydroxyl, aralkyl, heteroaryl, heteroaralkyl, haloalkyl, alkoxyl, —SR$^{20}$, —OR$^{20}$, —N(R$^{20}$)(R$^{20}$), —C(O)R$^{20}$, —CO$_2$R$^{20}$, —OC(O)R$^{20}$, —C(O)N(R$^{20}$)(R$^{20}$), —N(R$^{20}$)C(O)R$^{20}$, —N(R$^{20}$)C(O)N(R$^{20}$)(R$^{20}$), —S(O)R$^{20}$, —S(O)$_2$R$^{20}$, —S(O)$_2$N(R$^{20}$)(R$^{20}$), —N(R$^{20}$)S(O)$_2$R$^{20}$, —[(W)—C(O)]$_p$R$^{20}$, —[(W)—C(O)O]$_p$R$^{20}$, —[(W)—OC(O)]$_p$R$^{20}$, —[(W)—SO$_2$]$_p$R$^{20}$, —[(W)—N(R$^{20}$)SO$_2$]$_p$R$^{20}$, —[(W)—C(O)N(R$^{20}$)]$_p$R$^{20}$, —[(W)—O]$_p$R$^{20}$, [(W)—N(R$^{20}$)]$_p$R$^{20}$, or —[(W)—S]$_p$R$_{20}$;
each of R$^2$, R$^7$ and R$^{10}$ is independently H, alkyl, alkenyl, alkynyl, aryl, cycloalkyl, heterocycloalkyl, aralkyl, alkoxyl, aryloxy, acyloxy, halide, hydroxyl, amino, alkylamino, arylamino, acylamino, aralkylamino, alkylseleno, aralkylseleno, arylseleno, alkylthio, aralkylthio, arylthio, heteroaryl, or heteroaralkyl;
R$^3$ is H; or R$^2$ and R$^3$ taken together form a bond;
each of R$^4$ and R$^5$ independently is H, alkyl, alkenyl, alkynyl, aryl, cycloalkyl, nitrile, aralkyl, alkoxyl, aryloxy, acyloxy, halide, sulfhydryl, alkylthio, arylthio, aralkylthio, hydroxyl, amino, alkylamino, arylamino, acylamino, aralkylamino, heteroaryl, or heteroaralkyl; or R$^4$ and R$^5$ taken together form =O, =S, =N(R$^{20}$), =N—OR$^{20}$ or =N(N(R$^{20}$)$_2$);
R$^6$ is H, alkyl, alkenyl, alkynyl, aryl, cycloalkyl, heterocycloalkyl, or aralkyl; or R$^6$ and R$^{10}$ taken together form a bond;
each of R$^{11}$, R$^{12}$, R$^{14}$ and R$^{15}$ independently is H, alkyl, alkenyl, alkynyl, aryl, cycloalkyl, heterocycloalkyl, or aralkyl; or R$^{11}$ and R$^{12}$ taken together form a bond; or R$^7$ and R$^{14}$ taken together form a bond;

$R^{13}$ is H, alkyl, alkenyl, alkynyl, aryl, cycloalkyl, heterocycloalkyl, aralkyl, —C(O)R$^{20}$, —C(S)R$^{20}$, —CO$_2$R$^{20}$, —SO$_2$R$^{20}$, —C(O)N(R$^{20}$)(R$^{20}$); or —C(S)N(R$^{20}$)(R$^{20}$); or has the formula —[C(R$^{20}$)$_2$]$_q$—R$^{21}$;

$R^{20}$ independently for each occurrence is H, alkyl, alkenyl, alkynyl, aryl, cycloalkyl, heterocycloalkyl, aralkyl, heteroaryl, heteroaralkyl, or —[C(R)$_2$]$_q$—R$^{21}$, where each R is independently H or C1-C6 alkyl; or any two occurrences of $R^{20}$ can be taken together to form a 4-8 membered optionally substituted ring which contains 0-3 heteroatoms selected from N, O, S, and P;

$R^{21}$ independently for each occurrence is H, cycloalkyl, aryl, heteroaryl, heterocyclyl; alkoxyl, aryloxy, acyloxy, halide, sulfhydryl, alkylthio, arylthio, aralkylthio, hydroxyl, amino, acylamino, amido, or carbonyl-containing group;

$R^{22}$ independently for each occurrence is H, halide, ester, amide, or nitrile;

p is 0, 1, 2, 3, 4, 5, or 6;

q is 0, 1, 2, 3, 4, 5, or 6;

W is a diradical;

X is a bond or —C(R$^{22}$)$_2$—;

and each alkyl, alkenyl, alkynyl, aryl, cycloalkyl, heterocycloalkyl, aralkyl, heteroaryl, heteroaralkyl, whether alone or part of another group, is optionally substituted;

provided that when A is —N(R$^{13}$)—; B must be —(C═O)—, or —(C═S)—; and provided that when A is —(C═O)—, or —(C═S)—; B must be —N(R$^{13}$)—.

In some embodiments of the compounds of formula 15, A is —N(R$^{13}$)— and B is C═O. In other embodiments of the compounds of formula 15, B is —N(R$^{13}$)— and A is C═O.

In some of the foregoing embodiments of the compounds of formula 15, R$^{13}$ is H. In other such embodiments, R$^{13}$ is COOR$^{20}$ or SO$_2$R$^{20}$, wherein R$^{20}$ is C1-C6 alkyl or aryl-(C1-C6)-alkyl, and each alkyl and aryl is optionally substituted. In certain embodiments, when R$^{13}$ is COOR$^{20}$, R$^{20}$ is benzyl, methyl, ethyl, or tert-butyl.

In some of the foregoing embodiments of the compounds of formula 15, R$^{11}$ and R$^{12}$ are each H. In others, R$^{11}$ and R$^{12}$ are taken together to form a bond.

In some of the foregoing embodiments of the compounds of formula 15, R$^2$ and R$^3$ taken together form a bond. In other embodiments, R$^2$ and R$^3$ are both H.

In some of the foregoing embodiments of the compounds of formula 15, R$^4$ and R$^5$ are each H; in other such embodiments, R$^4$ and R$^5$ taken together form ═O.

In some of the foregoing embodiments of the compounds of formula 15, R$^7$ and R$^{10}$ are each H. In some of the foregoing embodiments of the compounds of formula 15, when R$^7$ is not H, R$^7$ and R$^{14}$ are taken together to form a bond. In other embodiments, when R$^{10}$ is not H, R$^{10}$ and R$^6$ are sometimes taken together to form a bond.

In some of the foregoing embodiments of the compounds of formula 15, R$^1$ is H. In other such embodiments, R$^1$ is COOR$^{20}$ or SO$_2$R$^{20}$, wherein R$^{20}$ is C1-C6 alkyl or aryl-(C1-C6)-alkyl, and each alkyl and aryl is optionally substituted. In certain embodiments, when R$^1$ is COOR$^{20}$, R$^{20}$ is benzyl, methyl, ethyl, or tert-butyl.

In some of the foregoing embodiments, the compound of formula 15, X is CH$_2$. In other such embodiments, X is a bond.

In some of the foregoing embodiments, p is 0 or 1 independently at each occurrence. In some such embodiments, p is 1.

In some embodiments, the compound of formula 15 is a compound of formula 21:

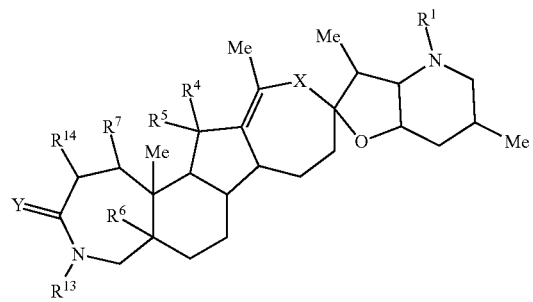

21 where R$^1$, R$^4$, R$^5$, R$^7$, R$^{14}$, R$^{13}$, R$^6$, R$^{20}$, and X are as defined above for formula 15, and Y is O or S; or a pharmaceutically acceptable salt thereof.

In some embodiments of the compound of formula 21, X is —CH$_2$—. In other embodiments, X is a bond.

In some of the foregoing embodiments of the compound of formula 21, Y is O. In some such embodiments, R$^6$ is H.

In some of the foregoing embodiments of the compounds of formula 21, R$^1$ is H. In other such embodiments, R$^1$ is COOR$^{20}$ or SO$_2$R$^{20}$, wherein R$^{20}$ is C1-C6 alkyl or aryl-(C1-C6)-alkyl, and each alkyl and aryl is optionally substituted. In certain embodiments, when R$^1$ is COOR$^{20}$, R$^{20}$ is benzyl, methyl, ethyl, or tert-butyl.

In some of the foregoing embodiments of the compounds of formula 21, R$^7$ and R$^{14}$ are both H. In other such embodiments, R$^7$ and R$^{14}$ are taken together to form a bond.

In some of the foregoing embodiments of the compound of formula 21, R$^4$ and R$^5$ are both H. In other such embodiments, R$^4$ and R$^5$ are taken together to form ═O.

In some of the foregoing embodiments of the compound of formula 21, R$^{13}$ is H or C1-C6 alkyl, such as methyl. In other such embodiments, R$^{13}$ is COOR$^{20}$ or SO$_2$R$^{20}$, wherein R$^{20}$ is C1-C6 alkyl or aryl-(C1-C6)-alkyl, and each alkyl and aryl is optionally substituted. In certain embodiments, when R$^{13}$ is COOR$^{20}$, R$^{20}$ is benzyl, methyl, ethyl, or tert-butyl. In some of the foregoing embodiments, p is 0 or 1 independently at each occurrence. In some such embodiments, p is 1.

In some of the foregoing embodiments, the compound of formula 21 has formula 23:

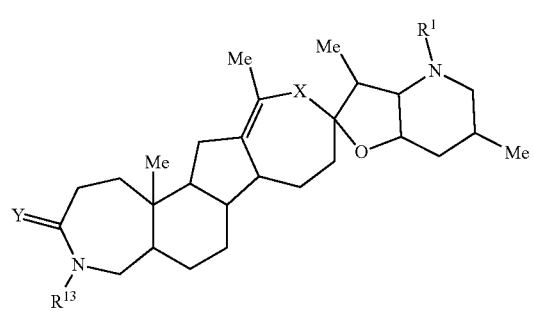

23 wherein R$^1$, R$^{13}$ and X are as defined for formula 15, and Y is O or S; or a pharmaceutically acceptable salt thereof.

In some embodiments of the compounds of formula 23, R$^1$ is H. In other such embodiments, R$^1$ is COOR$^{20}$ or SO$_2$R$^{20}$, wherein R$^{20}$ is C1-C6 alkyl or aryl-(C1-C6)-alkyl, and each alkyl and aryl is optionally substituted. In certain embodiments, when R¹ is COOR²⁰, R²⁰ is benzyl, methyl, ethyl, or tert-butyl.

In some of the foregoing embodiments of the compounds of formula 23, R¹³ is H. In other such embodiments, R¹³ is COOR²⁰ or SO₂R²⁰, wherein R²⁰ is C1-C6 alkyl or aryl-(C1-C6)-alkyl, and each alkyl and aryl is optionally substituted. In certain embodiments, when R¹³ is COOR²⁰, R²⁰ is benzyl, methyl, ethyl, or tert-butyl.

In some of the foregoing embodiments of the compounds of formula 23, X is CH₂. In other such embodiments, X is a bond.

In some of the foregoing embodiments of the compounds of formula 23, Y is O.

In some of the foregoing embodiments, p is 0 or 1 independently at each occurrence. In some such embodiments, p is 1.

In some embodiments, the compound of formula 15 is selected from:

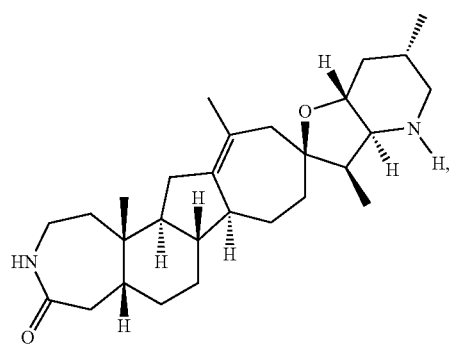

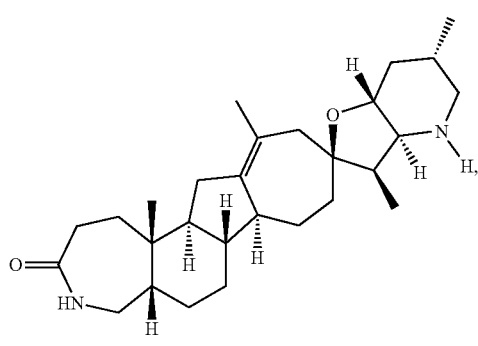

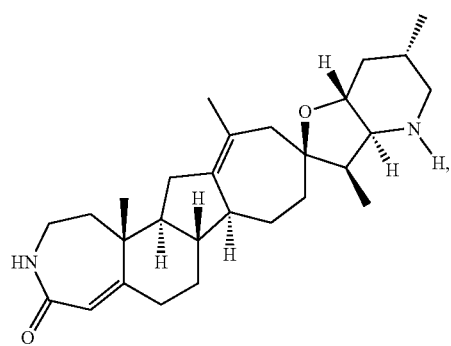

-continued

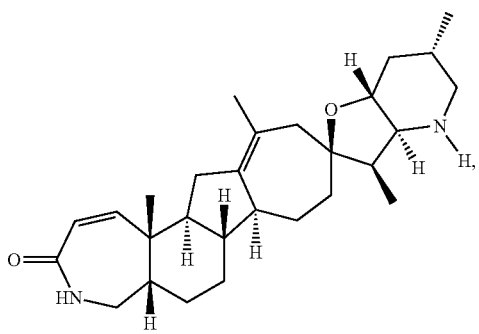

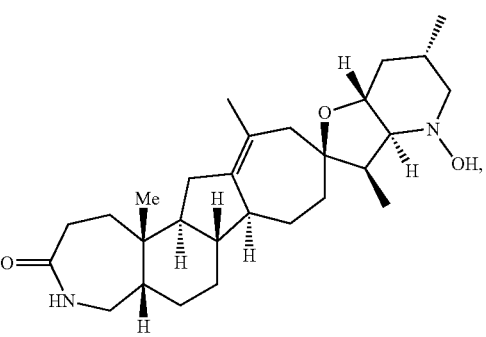

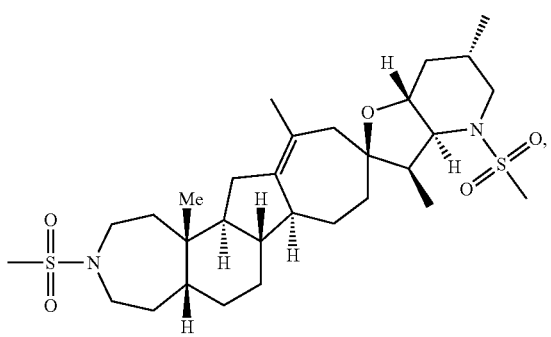

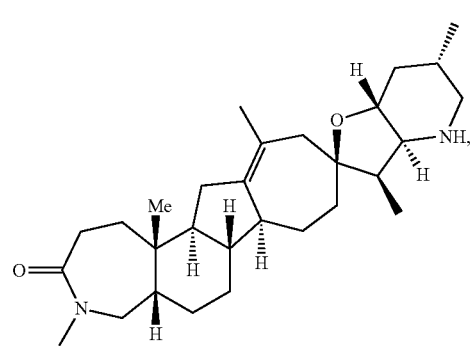

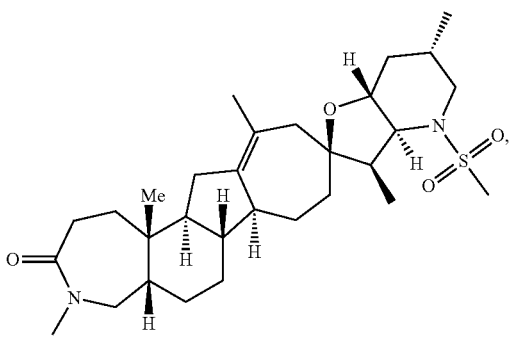

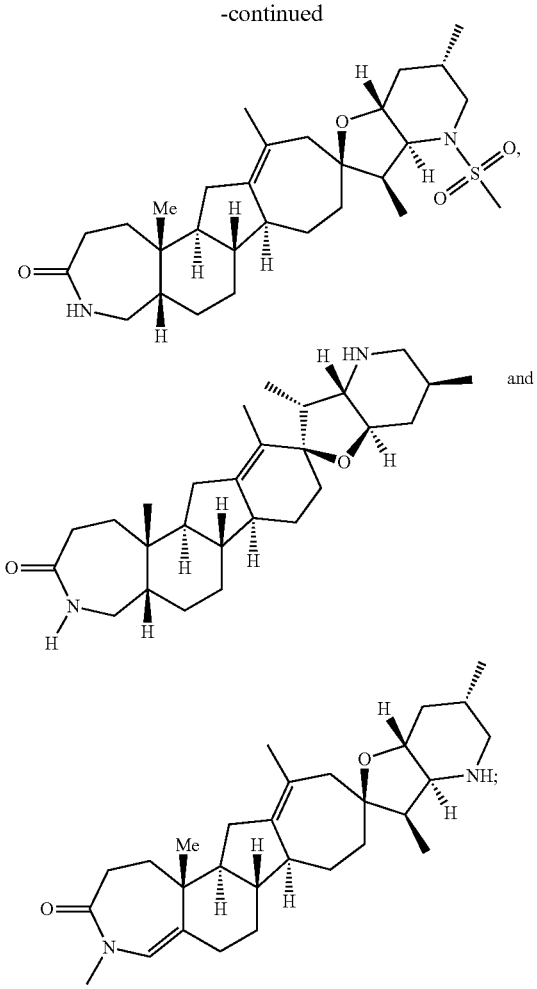

and their pharmaceutically acceptable salts.

The pharmaceutically acceptable salts of the compounds of the present invention include the conventional nontoxic salts or quaternary ammonium salts of the compounds, e.g., from non-toxic organic or inorganic acids. For example, such conventional nontoxic salts include those derived from inorganic acids such as hydrochloride, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like.

In other cases, the compounds of the present invention may contain one or more acidic functional groups and, thus, are capable of forming pharmaceutically-acceptable salts with pharmaceutically-acceptable bases. The term "pharmaceutically-acceptable salts" in these instances refers to the relatively non-toxic, inorganic and organic base addition salts of compounds of the present invention. These salts can likewise be prepared in situ in the administration vehicle or the dosage form manufacturing process, or by separately reacting the purified compound in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like. (See, for example, Berge, et al., supra)

In another aspect, the invention provides a pharmaceutical composition comprising at least one compound described in the above embodiments, admixed with at least one pharmaceutically acceptable excipient.

In another aspect, the invention provides a method of treating a condition mediated by the hedgehog pathway, including administering to a subject an effective amount of a compound described herein. The invention also provides a method of antagonizing the hedgehog pathway in a subject, including administering to the subject an effective amount of a compound described herein. The invention also provides a method of treating cancer in a subject, including administering to a subject a therapeutically effective amount of a compound described herein. Such cancers include cancers of the central nervous system and cancers of the gastrointestinal tract. The invention further provides a method of inhibiting activation of a hedgehog pathway in a patient diagnosed with a hyperproliferative disorder, including administering to the patient a compound described herein in an amount sufficient to reduce the activation of the hedgehog pathway in a cell of the patient.

In another aspect, the invention provides a method to treat a subject afflicted by excessive activity of a hedgehog pathway, which comprises administering to the subject at least one compound described in any of the above embodiments, or a pharmaceutically acceptable salt thereof, or a pharmaceutical composition thereof. In some embodiments, the subject is a subject diagnosed with a hyperproliferative disorder, and in some embodiments, the hyperproliferative disorder is cancer.

Synthesis of Steroidal Alkaloid Compounds

The steroidal alkaloid derivatives described above can be prepared directly from naturally occurring steroidal alkaloids or synthetic analogs thereof. In certain instances, the steroidal alkaloid starting materials can be cyclopamine or jervine. These steroidal alkaloids can be purchased commercially or extracted from *Veratrum californicum*.

In certain instances, the compounds of the present invention may contain a six membered nitrogen containing A-ring (see FIG. 1). These compounds may be accessed, as described below, by oxidative cleavage of the A-ring of a steroidal alkaloid with a double bond in the A-ring. Depending on the position of the double bond in the A-ring the site of cleavage and nitrogen incorporation into the ring may be changed. In the examples below, the double bond is conjugated to a ketone and upon exposure to sodium periodate and potassium permanganate the double is oxidatively cleaved and one carbon is removed from the ring. The resulting keto-ester may be treated with an amine and a reducing agent to form the 6-membered lactam. In the example, below ammonium acetate is used to form the 6-membered lactam. The resulting lactam may be further alkylated or in the alternative, a primary amine may be used to access tertiary lactams. The resulting lactams may be reduced to yield steroidal alkaloids with an amine in the A-ring.

In certain instances, the compounds of the present invention may contain a 7-membered nitrogen containing A-ring. These compounds may be formed directly from A-ring oxime-derivatives via the Beckman rearrangement. The rearranged product may be further derivatized by alkylation of the nitrogen of the amide, reduction of the amide to an amine, and the like. In the examples below an A-ring oxime is treated with MsCl and base to affect the Beckman rearrangement to afford secondary and tertiary A-ring expanded lactams.

In certain instances, the compounds of the present invention may contain a six or seven membered D-ring. Compounds with a 6-membered D-ring are accessible from certain natural products such as jervine or cyclopamine. Briefly, as illustrated by the example in Scheme A, the seven membered D-ring analogs may be accessed by cyclopropanating the D-ring of a suitable steroidal alkaloid followed by treating the resulting cyclopropanated product with a Lewis or Brønsted acid to catalyze a ring expansion rearrangement to yield the seven membered D-ring analogs.

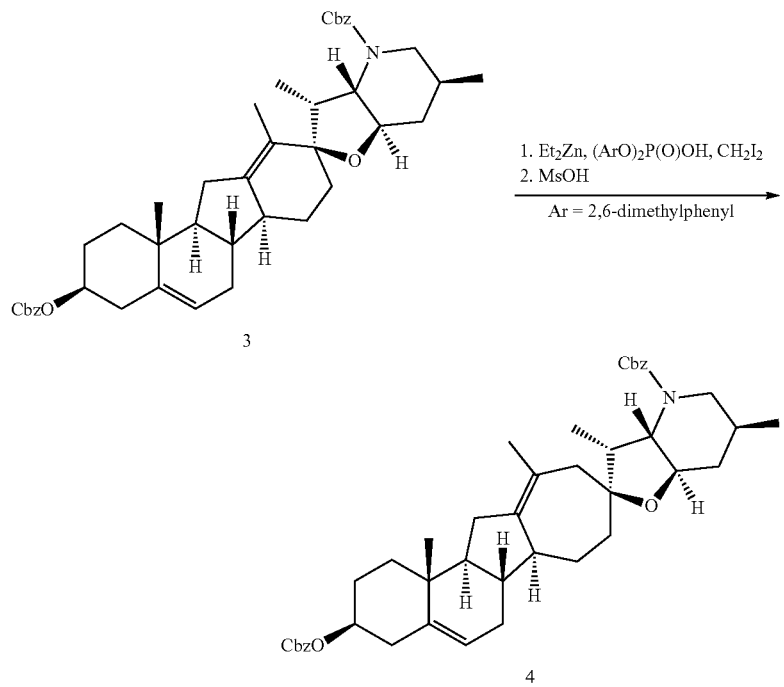

Scheme A. Exemplary formation of a 7-membered D-ring.

This ring expansion can be performed either before or after modifications of the A-ring are accomplished. These ring expanded analogs may be further functionalized using a variety of functionalization reactions known in the art. Representative examples include palladium coupling reactions to alkenylhalides or aryl halides, oxidations, reductions, reactions with nucleophiles, reactions with electrophiles, pericyclic reactions, installation of protecting groups, removal of protecting groups, and the like.

Pharmaceutical Compositions

The compounds disclosed herein or salts thereof may be formulated into composition suitable for administration, using one or more pharmaceutically acceptable carriers (additives) and/or diluents. The pharmaceutical compositions may be specially formulated for administration in solid or liquid form, including those adapted for the following: (1) oral administration, for example, drenches (aqueous or nonaqueous solutions or suspensions), tablets, e.g., those targeted for buccal, sublingual, and systemic absorption, capsules, boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; (8) pulmonarily, or (9) nasally.

Examples of suitable aqueous and nonaqueous carriers which may be employed in the pharmaceutical compositions include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents, dispersing agents, lubricants, and/or antioxidants. Prevention of the action of microorganisms upon the compounds disclosed herein may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Methods of preparing these formulations or compositions include the step of bringing into association a compound with the carrier and, optionally, one or more accessory ingredients. In general, the formulations are prepared by uniformly and intimately bringing into association a compound with liquid carriers, or finely divided solid carriers, or both, and then, if necessary, shaping the product.

When the compounds disclosed herein are administered as pharmaceuticals, to humans and animals, they can be given per se or as a pharmaceutical composition containing, for example, about 0.1 to 99%, or about 10 to 50%, or about 10 to 40%, or about 10 to 30, or about 10 to 20%, or about 10 to 15% of active ingredient in combination with a pharmaceutically acceptable carrier.

Actual dosage levels of the active ingredients in the pharmaceutical compositions may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound employed, or the ester, salt or amide thereof, the route of administration, the time of administration, the rate of excretion or metabolism of the particular compound being employed, the rate and extent of absorption, the duration of the treatment, other drugs, compounds and/or materials used in combination with the particular compound employed, the age, sex, weight, condition, general health and prior medical history of the patient being treated, and like factors well known in the medical arts.

In general, a suitable daily dose of a compound disclosed herein will be that amount of the compound which is the lowest dose effective to produce a therapeutic effect. Such an effective dose will generally depend upon the factors described above. Generally, oral, intravenous and subcutaneous doses of the compounds for a patient, when used for the indicated effects, will range from about 0.0001 to about 200 mg, or about 0.001 to about 100 mg, or about 0.01 to about 100 mg, or about 0.1 to about 100 mg per, or about 1 to about 50 mg per kilogram of body weight per day.

The compounds can be administered daily, every other day, three times a week, twice a week, weekly, or bi-weekly. The dosing schedule can include a "drug holiday," i.e., the drug can be administered for two weeks on, one week off, or three weeks on, one week off, or four weeks on, one week off, etc., or continuously, without a drug holiday. The compounds can be administered orally, intravenously, intraperitoneally, topically, transdermally, intramuscularly, subcutaneously, intranasally, sublingually, or by any other route. The subject receiving this treatment is any animal in need, including primates, in particular humans, and other mammals such as equines, cattle, swine and sheep; and poultry and pets in general.

Methods of Treatment

Hedgehog signaling is essential in many stages of development, especially in formation of left-right symmetry. Loss or reduction of hedgehog signaling leads to multiple developmental deficits and malformations, one of the most striking of which is cyclopia. Many tumors and proliferative conditions have been shown to depend on the hedgehog pathway. The growth of such cells and survival can be affected by treatment with the compounds disclosed herein. Recently, it has been reported that activating hedgehog pathway mutations occur in sporadic basal cell carcinoma (Xie et al. (1998) *Nature* 391: 90-2) and primitive neuroectodermal tumors of the central nervous system (Reifenberger et al. (1998) *Cancer Res* 58: 1798-803). Uncontrolled activation of the hedgehog pathway has also been shown in numerous cancer types such as GI tract cancers including pancreatic, esophageal, gastric cancer (Berman et al. (2003) *Nature* 425: 846-51, Thayer et al. (2003) *Nature* 425: 851-56) lung cancer (Watkins et al. (2003) *Nature* 422: 313-317, prostate cancer (Karhadkar et al (2004) *Nature* 431: 707-12, Sheng et al. (2004) *Molecular Cancer* 3: 29-42, Fan et al. (2004) *Endocrinology* 145: 3961-70), breast cancer (Kubo et al. (2004) *Cancer Research* 64: 6071-74, Lewis et al. (2004) *Journal of Mammary Gland Biology and Neoplasia* 2: 165-181) and hepatocellular cancer (Sicklick et al. (2005) ASCO conference, Mohini et al. (2005) AACR conference).

For example, small molecule inhibition of the hedgehog pathway has been shown to inhibit the growth of basal cell carcinoma (Williams, et al., 2003 PNAS 100: 4616-21), medulloblastoma (Berman et al., 2002 Science 297: 1559-61), pancreatic cancer (Berman et al., 2003 Nature 425: 846-51), gastrointestinal cancers (Berman et al., 2003 Nature 425: 846-51, published PCT application WO 05/013800), esophageal cancer (Berman et al., 2003 Nature 425: 846-51), lung cancer (Watkins et al., 2003. Nature 422: 313-7), and prostate cancer (Karhadkar et al., 2004. Nature 431: 707-12).

In addition, it has been shown that many cancer types have uncontrolled activation of the hedgehog pathway, for example, breast cancer (Kubo et al., 2004. Cancer Research 64: 6071-4), heptacellular cancer (Patil et al., 2005. 96$^{th}$ Annual AACR conference, abstract #2942 Sicklick et al., 2005. ASCO annual meeting, abstract #9610), hematological malignancies (Watkins and Matsui, unpublished results), basal carcinoma (Bale & Yu, 2001. Human Molec. Genet. 10:757-762 Xie et al., 1998 Nature 391: 90-92), medulloblastoma (Pietsch et al., 1997. Cancer Res. 57: 2085-88), and gastric cancer (Ma et al., 2005 Carcinogenesis May 19, 2005 (Epub)). In addition, investigators have found that small molecule inhibition of the hedgehog pathway has been shown to ameliorate the symptoms of psoriasis (Tas, et al., 2004 Dermatology 209: 126-131). As shown in the Examples, the compounds disclosed herein have been shown to modulate the hedgehog pathway, and selected compounds have been shown to inhibit tumor growth. It is therefore believed that these compounds can be useful to treat a variety of hyperproliferative disorders, such as various cancers.

Proliferative disorders that can be treated using the methods disclosed herein include: lung cancer (including small cell lung cancer and non small cell lung cancer), other cancers of the pulmonary system, medulloblastoma and other brain cancers, pancreatic cancer, basal cell carcinoma, breast cancer, prostate cancer and other genitourinary cancers, gastrointestinal stromal tumor (GIST) and other cancers of the gastrointestinal tract, colon cancer, colorectal cancer, ovarian cancer, cancers of the hematopoietic system (including multiple myeloma, acute lymphocytic leukemia, acute myelocytic leukemia, chronic myelocytic leukemia, chronic lymphocytic leukemia, Hodgkin lymphoma, and non-Hodgkin lymphoma, and myelodysplastic syndrome), polycythemia Vera, Waldenstrom's macroglobulinemia, heavy chain disease, soft-tissue sarcomas, such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, squamous cell carcinoma, basal cell carcinoma, melanoma, and other skin cancers, adenocarcinoma, sweat gland carcinoma, sebaceous gland carcinoma, papillary carcinoma, papillary adenocarcinomas, stadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, uterine cancer, testicular cancer, bladder carcinoma, and other genitourinary cances, epithelial carcinoma, glioma, astrocytoma, medulloblastoma, craniopharyngioma, ependymoma, pinealoma, hemangioblastoma, acoustic neuroma, oligodendroglioma, meningioma, neuroblastoma, retinoblastoma, endometrial cancer, follicular lymphoma, diffuse large B-cell lymphoma, mantle cell lymphoma, hepatocellular carcinoma, thyroid cancer, gastric cancer, esophageal cancer, head and neck cancer, small cell cancers, essential thrombocythemia, agnogenic myeloid metaplasia, hypereosinophilic syndrome, systemic mastocytosis, familiar hypereosinophilia, chronic eosinophilic leukemia, thyroid cancer, neuroendocrine cancers, and carcinoid tumors. Additional disorders include Gorlin's syndrome and psoriasis The subject receiving this treatment is any animal in need, including primates, in particular humans, and other mammals such as equines, cattle, swine and sheep; and poultry and pets in general.

The hedgehog inhibitors disclosed herein can be combined with other cancer treatments. For example, they can be combined with surgical treatments; radiation; biotherapeutics (such as interferons, cytokines—e.g. Interferon α, Interferon γ, and tumor necrosis factor, hematopoietic growth factors, monoclonal serotherapy, vaccines and immunostimulants); antibodies (e.g. Avastin, Erbitux, Rituxan, and Bexxar); endocrine therapy (including peptide hormones, corticosteroids, estrogens, androgens and aromatase inhibitors); anti-estrogens (e.g. Tamoxifen, Raloxifene, and Megestrol); LHRH agonists (e.g. goscrelin and Leuprolide acetate); anti-androgens (e.g. flutamide and Bicalutamide); gene therapy; bone marrow transplantation; photodynamic therapies (e.g. vertoporfin (BPD-MA), Phthalocyanine, photosensitizer Pc4, and Demethoxy-hypocrellin A (2BA-2-DMHA)); and chemotherapeutics.

Examples of chemotherapeutics include gemcitabine, methotrexate, taxol, mercaptopurine, thioguanine, hydroxyurea, cytarabine, cyclophosphamide, ifosfamide, nitrosoureas, cisplatin, carboplatin, mitomycin, dacarbazine, procarbizine, etoposides, prednisolone, dexamethasone, cytarbine, campathecins, bleomycin, doxorubicin, idarubicin, daunorubicin, dactinomycin, plicamycin, mitoxantrone, asparaginase, vinblastine, vincristine, and vinorelbine. Additional agents include nitrogen mustards (e.g. cyclophosphamide, Ifosfamide, Trofosfamide, Chlorambucil, Estramustine, and Melphalan), nitrosoureas (e.g. carmustine (BCNU) and Lomustine (CCNU)), alkylsulphonates (e.g. busulfan and Treosulfan), triazenes (e.g. Dacarbazine and Temozolomide), platinum containing compounds (e.g. Cisplatin, Carboplatin, and oxaliplatin), vinca alkaloids (e.g. vincristine, Vinblastine, Vindesine, and Vinorelbine), taxoids (e.g. paclitaxel and Docetaxol), epipodophyllins (e.g. etoposide, Teniposide, Topotecan, 9-Aminocamptothecin, Camptoirinotecan, Crisnatol, Mytomycin C, and Mytomycin C), anti-metabolites, DHFR inhibitors (e.g. methotrexate and Trimetrexate), IMP dehydrogenase Inhibitors (e.g. mycophenolic acid, Tiazofurin, Ribavirin, and EICAR), ribonucleotide reductase Inhibitors (e.g. hydroxyurea and Deferoxamine), uracil analogs (e.g. Fluorouracil, Floxuridine, Doxifluridine, Ratitrexed, and Capecitabine), cytosine analogs (e.g. cytarabine (ara C), Cytosine arabinoside, and Fludarabine), purine analogs (e.g. mercaptopurine and Thioguanine), Vitamin D3 analogs (e.g. EB 1089, CB 1093, and KH 1060), isoprenylation inhibitors (e.g. Lovastatin), dopaminergic neurotoxins (e.g. 1-methyl-4-phenylpyridinium ion), cell cycle inhibitors (e.g. staurosporine), actinomycins (e.g. Actinomycin D and Dactinomycin), bleomycins (e.g. bleomycin A2, Bleomycin B2, and Peplomycin), anthracyclines (e.g. daunorubicin, Doxorubicin (adriamycin), Idarubicin, Epirubicin, Pirarubicin, Zorubicin, and Mitoxantrone), MDR inhibitors (e.g. verapamil), $Ca^{2+}$ ATPase inhibitors (e.g. thapsigargin), imatinib, thalidomide, lenalidomide, erlotinib, gefitinib, sorafenib, and sunitinib, and proteasome inhibitors, including bortezomib.

When the hedgehog inhibitors disclosed herein are administered in combination with other treatments, such as additional therapeutics or with radiation or surgery, the doses of each agent or therapy will in most instances be lower than the corresponding dose for single-agent therapy. Also, in general, the hedgehog inhibitors described herein and the second therapeutic agent do not have to be administered in the same pharmaceutical composition, and may, because of different physical and chemical characteristics, be administered by different routes. For example, one compound can be administered orally, while the second therapeutic is administered intravenously. The determination of the mode of administration and the advisability of administration, where possible, in the same pharmaceutical composition, is well within the knowledge of the skilled clinician. The initial administration can be made according to established protocols known in the art, and then, based upon the observed effects, the dosage, modes of administration and times of administration can be modified by the skilled clinician.

The hedgehog inhibitor and the second therapeutic agent and/or radiation may be administered concurrently (e.g., simultaneously, essentially simultaneously or within the same treatment protocol) or sequentially (i.e., one followed by the other, with an optional time interval in between), depending upon the nature of the proliferative disease, the condition of the patient, and the actual choice of second therapeutic agent and/or radiation to be administered.

If the hedgehog inhibitor, and the second therapeutic agent and/or radiation are not administered simultaneously or essentially simultaneously, then the optimum order of administration may be different for different conditions. Thus, in certain situations the hedgehog inhibitor may be administered first followed by the administration of the second therapeutic agent and/or radiation; and in other situations the second therapeutic agent and/or radiation may be administered first followed by the administration of a hedgehog inhibitor. This alternate administration may be repeated during a single treatment protocol. The determination of the order of administration, and the number of repetitions of administration of each therapeutic agent during a treatment protocol, is well within the knowledge of the skilled physician after evaluation of the disease being treated and the condition of the patient. For example, the second therapeutic agent and/or radiation may be administered first, especially if it is a cytotoxic agent, and then the treatment continued with the administration of a hedgehog inhibitor followed, where determined advantageous, by the administration of the second therapeutic agent and/or radiation, and so on until the treatment protocol is complete.

EXEMPLIFICATION

The invention now being generally described, it will be more readily understood by reference to the following examples, which are included merely for purposes of illustration of certain aspects and embodiments of the present invention, and are not intended to limit the invention.

Example 1

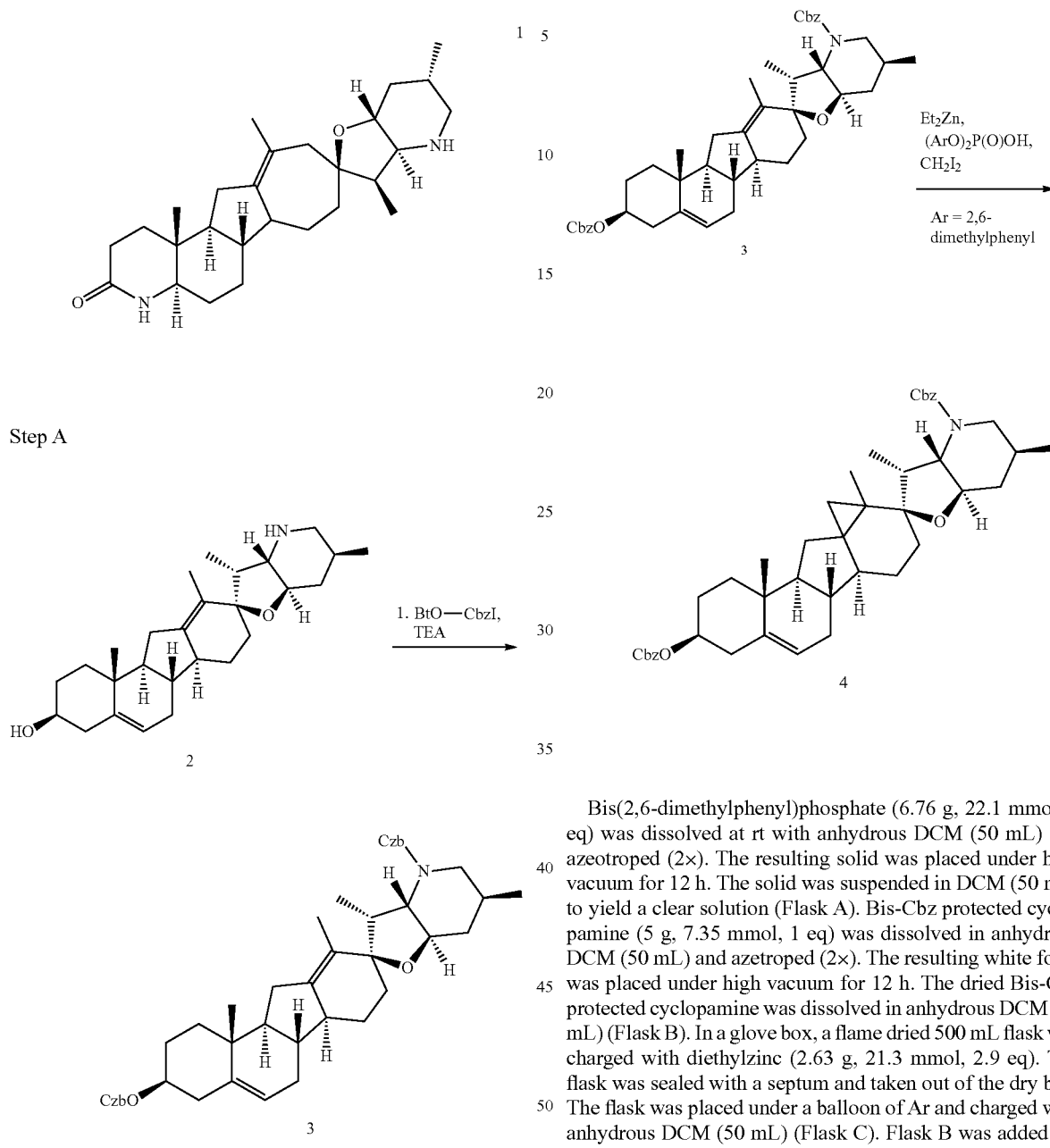

Step A

Cyclopamine 2 (5.02 g, 12.2 mmol, 1.0 eq) was dissolved in anhydrous pyridine (25 mL) DMAP (300 mg, 2.44 mmol, 0.2 eq.) and triethyl amine (5.5 mL, 39.1 mmol, 3.2 eq) were added, followed by BtO-Cbz (10.5 g, 39.1 mmol, 3.2 eq) and the mixture was heated at 40° C. for 2 h. The mixture was cooled to rt, treated with 30 mL water, heated to get a homogeneous solution and allowed to cool to rt. The white, precipitate that formed was collected by filtration, the filter cake was washed with portions of water (3×50 mL), and dried in air to afford 9.53 g of crude material which crystallized from toluene/heptanes (1:9, 70 mL) to give 6.75 g of the desired product.

Step B

Bis(2,6-dimethylphenyl)phosphate (6.76 g, 22.1 mmol, 3 eq) was dissolved at rt with anhydrous DCM (50 mL) and azeotroped (2×). The resulting solid was placed under high vacuum for 12 h. The solid was suspended in DCM (50 mL) to yield a clear solution (Flask A). Bis-Cbz protected cyclopamine (5 g, 7.35 mmol, 1 eq) was dissolved in anhydrous DCM (50 mL) and azetroped (2×). The resulting white foam was placed under high vacuum for 12 h. The dried Bis-Cbz protected cyclopamine was dissolved in anhydrous DCM (15 mL) (Flask B). In a glove box, a flame dried 500 mL flask was charged with diethylzinc (2.63 g, 21.3 mmol, 2.9 eq). The flask was sealed with a septum and taken out of the dry box. The flask was placed under a balloon of Ar and charged with anhydrous DCM (50 mL) (Flask C). Flask B was added via cannula to flask C over 15 min. The reaction was allowed to stir at rt for 20 min A clear solution was obtained. Flask A was transferred to the reaction flask C via cannula over 10 min. The reaction was stirred for an additional 5 min resulting in a slightly hazy yellow solution. Diiodomethane (1.78 mL, 22.1 mmol, 3 eq) was added at rt over 1 min. The reaction was allowed to stir for 24 h. The reaction was quenched by the addition of a saturated aqueous $NH_4Cl$ solution. The layers were separated and the aqueous layers were back extracted with DCM. The combined organic layers were washed with saturated aqueous $NH_4Cl$ solution (1×), 5% $NaHCO_3$ (2×), 10% $Na_2SO_3$ (1×). The organic solvent was dried over $Na_2SO_4$, filtered, and evaporated to dryness to give a foamy solid. Purification by flash silica gel chromatography (hexanes/EtOAc 95:5 to 8:2) yielded 3.8 g of the desired material.

Step C

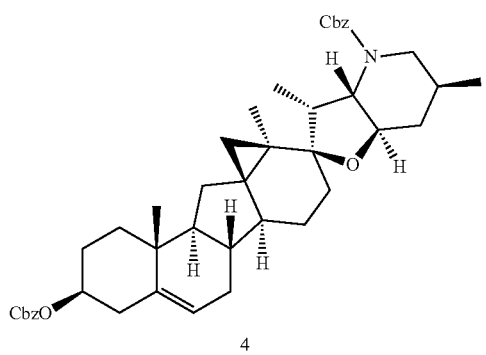

4

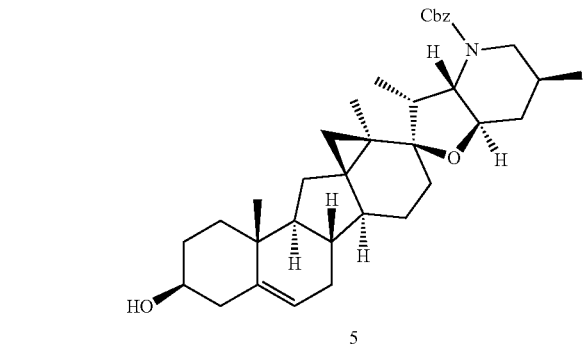

5

A round-bottom flask was charged with Bis-Cbz-protected cyclopropylcyclopamine (2 g, 2.88 mmol, 1 eq), MeOH (15 mL), and THF (5 mL) and vigorously stirred with 2N NaOH (2 mL) at 55° C. for 3 h. The THF and MeOH were removed under reduced pressure and the residue was extracted with EtOAc (3×). The combined organic layers were washed with brine, dried over Na$_2$SO$_4$, filtered, and evaporated to dryness to give a foamy solid. Purification by flash silica gel chromatography (hexanes/EtOAc 9:1 to 8:2) to afford 1.1 g of the desired material.

Step D

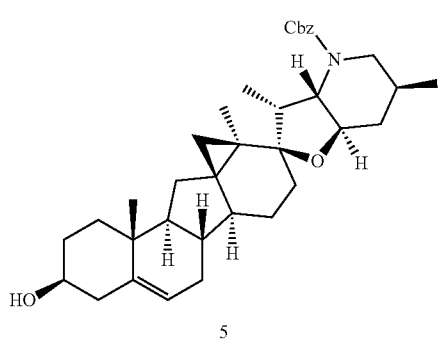

5

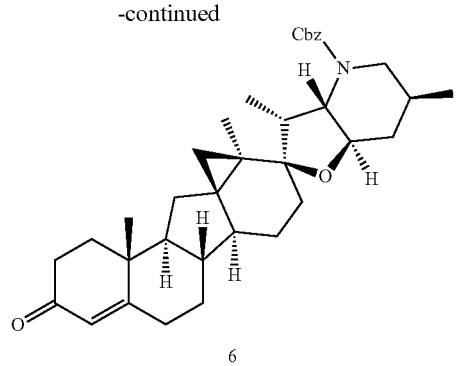

6

A round-bottom flask was charged with N-Cbz-cyclopropylcyclopamine (2.3 g, 4.1 mmol, 1 eq), Al(OBu)$_3$ (1.4 g, 5.76 mmol, 1.4 eq), toluene (30 mL), and 2-butanone (30 mL). The mixture was heated at 75° C. under Ar for 10 h. The reaction was quenched by the addition of an aqueous 20% Rochelle's salt solution. The biphasic mixture was stirred at 40° C. for 20 min. The layers were separated and the aqueous layer was extracted three times with EtOAc/toluene (1:1). The combined organic layers were washed with 20% Rochelle's salt, dried over Na$_2$SO$_4$, filtered, and concentrated to dryness by two successive azeotropic distillations with heptanes. The crude material was purified using silica gel flash chromatography (hexanes/EtOAc 4:1) to afford 859 mg of the desired product.

Step E

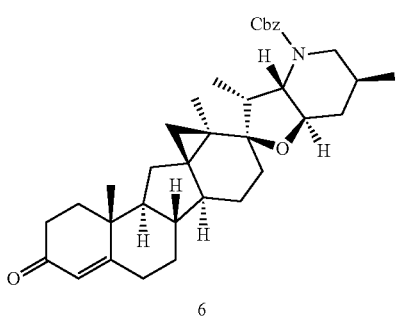

6

1. NaIO$_4$, KMnO$_4$
2. TMSCHN$_2$

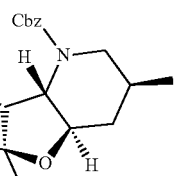

7

The enone derivative (350 mg, 0.63 mmol, 1 eq) was dissolved in t-BuOH (5 mL) then a solution of Na$_2$CO$_3$ (100 mg, 0.94 mmol, 1.5 eq) in water (5 mL) was added. The mixture was heated to 80° C. and charged with a solution of NaIO$_4$ (0.94 g, 4.4 mmol, 7 eq) and KMnO$_4$ (7 mg, 0.043 mmol, 0.07 eq) in water (5 mL). After 60 min, the mixture was cooled to rt. The basic mixture was acidified with 2N HCl, and extracted with EtOAc (3×). The combined organic layers were washed with saturated aqueous NH₄Cl, dried over Na₂SO₄, filtered and concentrated to dryness. The material was chased a couple times with MTBE. The material (373 mg) was dissolved in toluene/MeOH (10 mL; 4:1, HPLC grade) and treated with of 2M TMSCHN₂ in hexanes (630 μL, 1.2 mmol, 2 eq). Bubbling was observed and the bright yellow color persisted. Nitrogen was bubbled through the solution then the solution was concentrated to dryness. The crude material (366 mg) was purified using silica gel flash chromatography (hexanes/EtOAc 95:5 to 4:1) to afford the desired material as a white foam (245 mg).

Step F

The compound 7 (237 mg, 0.4 mmol, 1 eq) was dissolved in MeOH (5 mL) and treated with NH₄OAc (1.2 g, 16 mmol, 40 eq) and sodium cyanoborohydride (251 mg, 4 mmol, 10 eq) at rt for 3 h. Then, NH₄OAc (600 mg, 8 mmol, 20 eq) was added to the reaction mixture, which was warmed to 50° C. and stirred for 4 h. Saturated aqueous NaHCO₃ was added and MeOH was distilled undr reduced pressure. The residue was extracted with EtOAc (3×). The combined organic layers were washed with 1N NaOH (1×), then saturated NH₄Cl (1×), then the layers clearly separated. The organic layer was dried over Na₂SO₄, filtered, and concentrated to dryness. The crude material (257 mg) was purified using flash silica gel flash chromatography (hexanes/EtOAc 1:9 to 100% EtOAc) to give 5β-reduced lactam (82 mg compound 8) followed by 5α-reduced lactam (89 mg, compound 9).

Step G

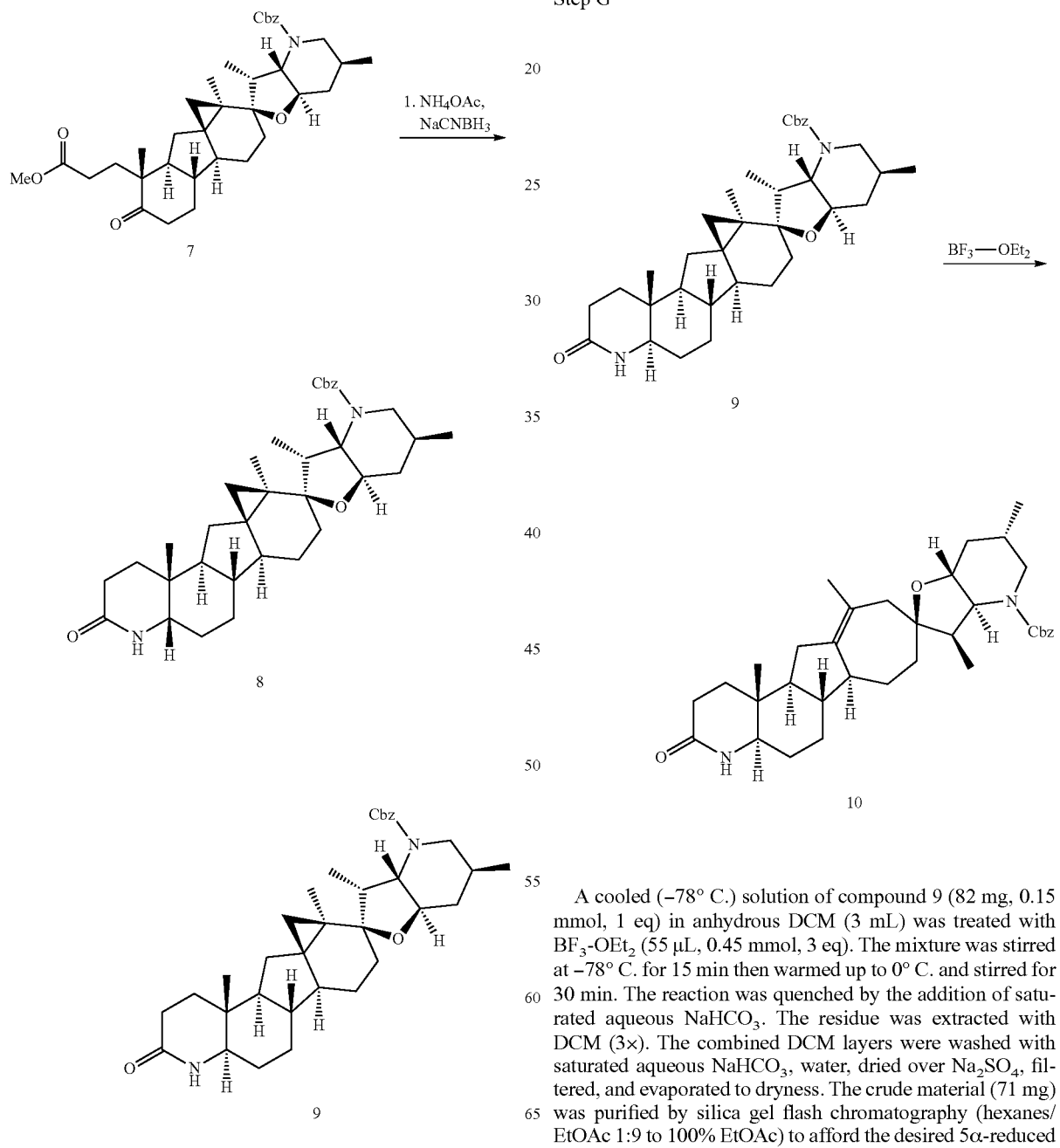

A cooled (−78° C.) solution of compound 9 (82 mg, 0.15 mmol, 1 eq) in anhydrous DCM (3 mL) was treated with BF₃-OEt₂ (55 μL, 0.45 mmol, 3 eq). The mixture was stirred at −78° C. for 15 min then warmed up to 0° C. and stirred for 30 min. The reaction was quenched by the addition of saturated aqueous NaHCO₃. The residue was extracted with DCM (3×). The combined DCM layers were washed with saturated aqueous NaHCO₃, water, dried over Na₂SO₄, filtered, and evaporated to dryness. The crude material (71 mg) was purified by silica gel flash chromatography (hexanes/EtOAc 1:9 to 100% EtOAc) to afford the desired 5α-reduced lactam product as solidifying oil (48 mg).

Step H

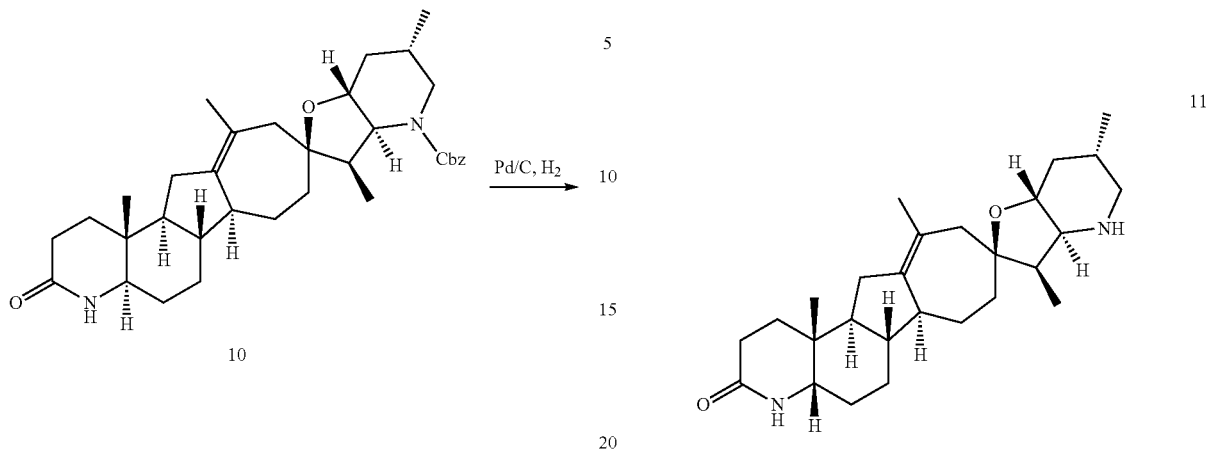

Compound 10 (42 mg, 0.075 mmol, 1 equiv.) was dissolved in EtOAc (3 mL) and treated with Pd/C 10% (8 mg, wet, Aldrich Degussa type E101 lot 08331KC). The flask was sealed and purged with hydrogen (3×) and stirred for 10 h under 1 atm of hydrogen. The mixture was filtered through a 0.2 micron AcrosDisc filter to give 46 mg of crude material. Purification by silica gel flash chromatography (DCM to DCM/MeOH 92:8) afforded 20 mg of pure material ([M+H]= 427.4 m/z).

Example 2

Compound 11 was synthesized according to the procedure described in example 1, using compound 8 in place of compound 9 in steps G and H.

Example 3

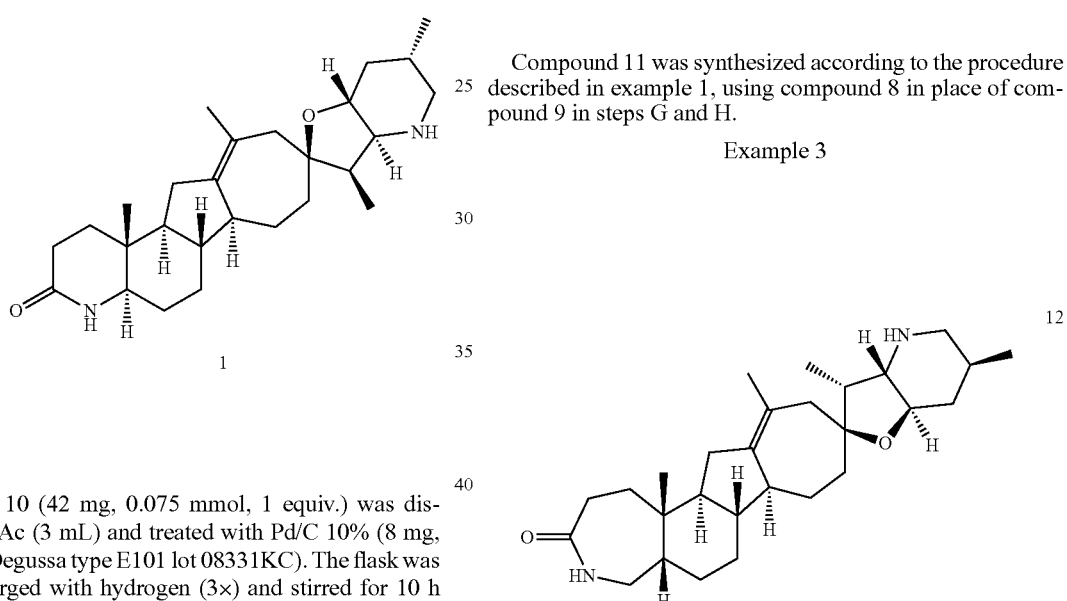

Step A

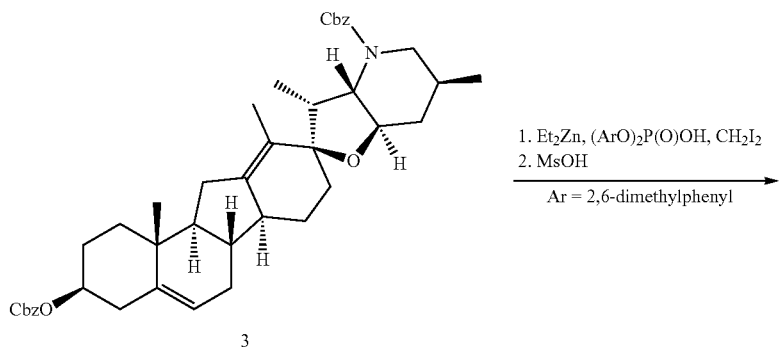

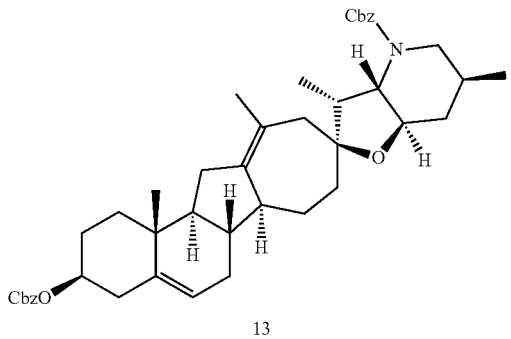

13

To a solution of diethyl zinc (572 mg, 482 µL, 4.63 mmol, 3 eq) in DCM (5.0 mL) at −20° C. was added a solution of bis-(2,6-Dimethylphenyl)phosphoric acid (1.42 g, 4.63 mmol, 3 eq) in DCM (15 mL) while maintaining the reaction temperature below −8° C. The solution was aged for 15 min. at 0° C., neat diiodomethane (1.24 g, 374 µL, 3 eq) was added, and the mixture was aged for 15 min. at 0° C. before adding a solution of (Bis-CBz-cyclopamine, 1.05 g, 1.54 mmol, 1.0 eq), in DCM (10 mL). The cooling bath was replaced by a water bath at rt and maintained at rt for 4.5 h. The mixture was cooled to −76° C. with a dry ice-acetone bath and treated drop wise with methanesulfonic acid DCM solution (0.6 mL 50% v/v solution 4.63 mmol, 3.0 eq) while maintaining the reaction temperature below −74° C. The mixture was aged for 15-20 min. and quenched drop wise with morpholine (2.69 g, 2.70 mL, 20 eq) maintaining the reaction temperature below −65° C. The cooling bath was removed, the reaction mixture was stirred for 16-18 h., the white precipitate was filtered off, and the filtrate was successively washed with 2.0 m HCl (2×20 mL), satd. sodium bicarbonate (2×20 mL), water (2×20 mL) and brine (20 mL) It was then dried over magnesium sulfate, concentrated in vacuo to dryness and the crude was purified by silica gel flash chromatography (hexanes/EtOAc 17:3→4:1) to afford 924 mg (1.33 mmol, 86%) of the desired product.
Step B

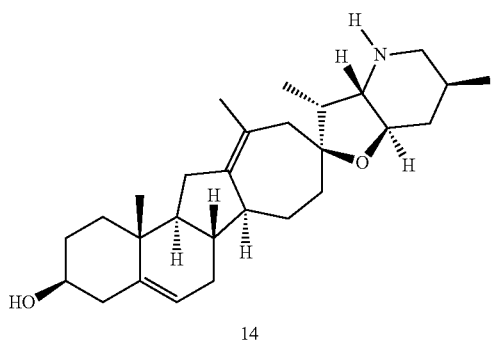

14

To a solution of compound 13 (4.05 g, 5.83 mmol, 1 eq) in a solution of EtOAc:toluene (2:1, 60 mL) was added 20% palladium hydroxide on carbon (823 mg, 0.583 mmol, 0.1 eq). The flask was evacuated and filled with hydrogen three times. The mixture was stirred under an atmosphere of hydrogen for 1 h. Neat ethylene diamine (0.38 mL) was added, and the mixture was stirred for 1 h., before the catalyst was filtered off. The filter cake was washed twice with EtOAc:toluene (2:1, 12 mL). The combined filtrates were washed with a 2% aqueous solution of ethylene diamine (3×20 mL), dried over sodium sulfate and concentrated in vacuo to give 2.46 g as a white crystalline solid.
Step C

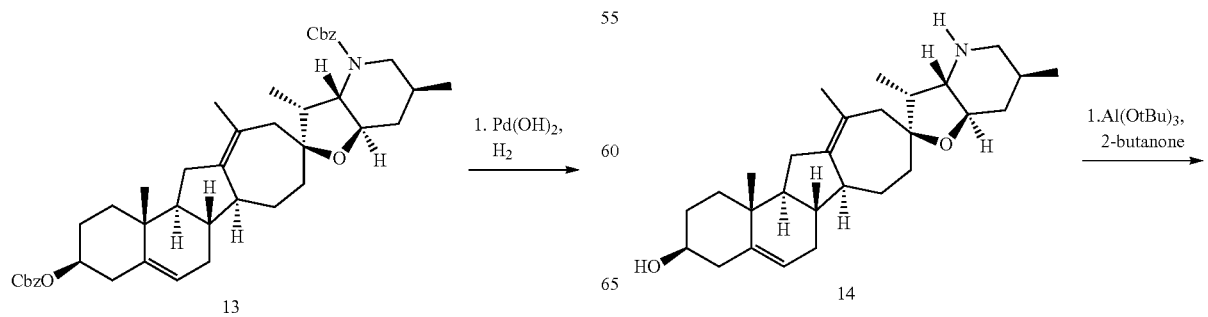

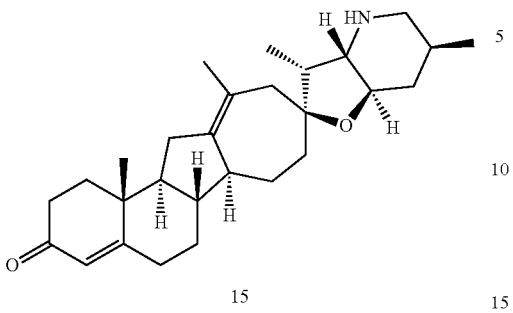

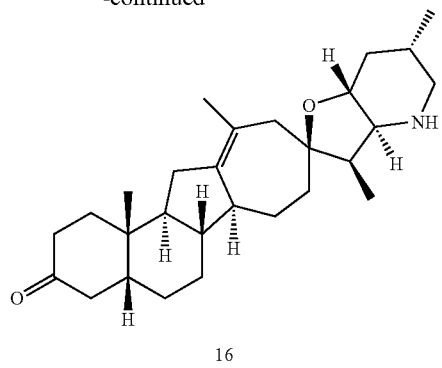

A round bottom flask was sequentially charged with the homo-allylic alcohol 14 (7.50 g, 17.6 mmol, 1 eq), aluminum tert-butoxide (6.10 g, 24.8 mmol, 1.4 eq), anhydrous toluene (115 mL), and 2-butanone (90 g, 1.24 mol, 7 eq). The suspension was heated under a nitrogen atmosphere to 75° C. for 16 h. The reaction temperature was then allowed to cool to 49° C. Aqueous 20% (w/w) potassium sodium tartrate solution (226 g) was added to the stirred suspension. The suspension was stirred at rt for 3.5 h. The layers were separated. The organic layer was washed with aqueous 20% Rochelle's salt (2×250 mL) and water (225 mL), then dried over sodium sulfate and filtered. The residue was rinsed with toluene (30 mL) and discarded. The combined organics were concentrated to dryness. Residual reaction solvents were removed from the material by concentrating from 2-propanol (250 mL added portion-wise) to a final solution mass of 44 g. Solvent exchange from 2-propanol to n-heptane (275 mL added portion-wise) to a final solution mass of 41 g fully precipitated the desired product. The suspension was diluted with additional n-heptane (40 mL), stirred at rt for 1 h, and filtered. The product was washed with n-heptane (17 mL) and dried to afford 5.4 g of the desired product.

Step D

A round-bottom flask was charged with starting material (110 mg, 0.26 mmol, 1 eq) and 10% palladium on carbon (106 mg). The solids were suspended in pyridine (4 mL). The suspension was placed under hydrogen atmosphere (1 atm) and the mixture was stirred overnight at rt. The reaction mixture was filtered through celite and the filtrate concentrated in vacuo. The crude material was purified using silica gel flash chromatography (MeOH/DCM 5:95) to afford 93 mg of the desired compound.

Step E

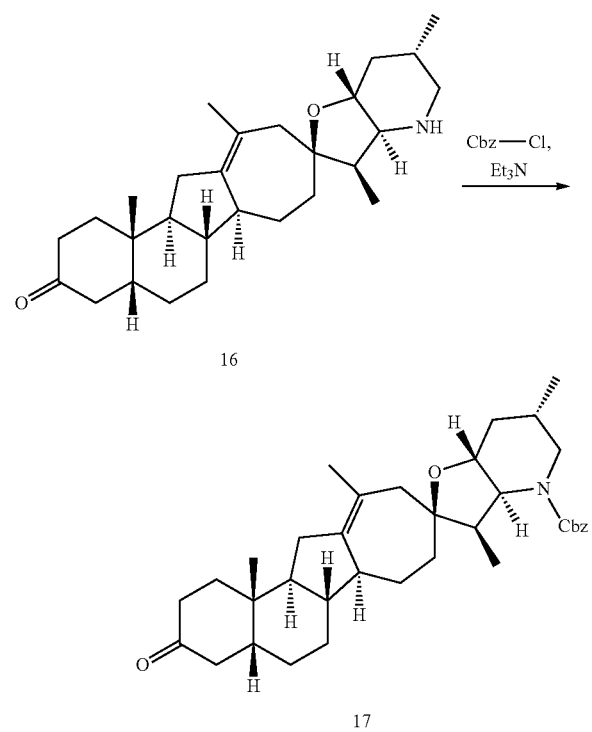

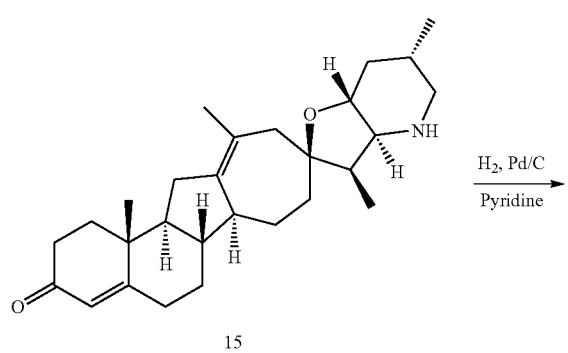

A round-bottom flask was charged with compound 16 (4.23 g, 9.94 mmol, 1 eq) and THF (60 mL). Triethylamine (6.92 mL, 49.7 mmol, 5.0 eq) and benzyl chloroformate (1.54 mL, 10.93 mmol, 1.1 eq) were added and the mixture was stirred for 1 h at rt. The reaction mixture was partitioned between saturated aqueous bicarbonate (100 mL) and EtOAc (100 mL). The phases were separated and the organics were dried ($Na_2SO_4$) and concentrated to dryness. The crude material was purified using silica gel flash chromatography (EtOAc/Hexanes 2:98→14:86) to give 3.75 g of material.

Step F

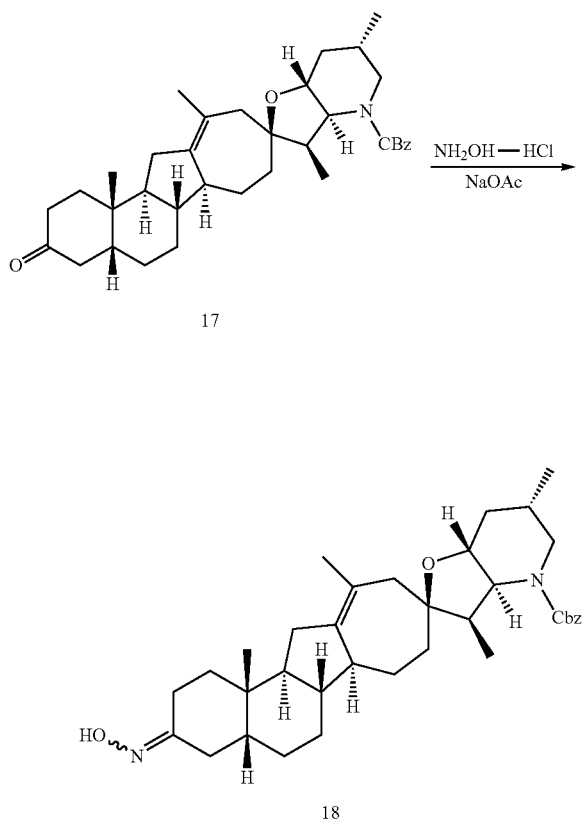

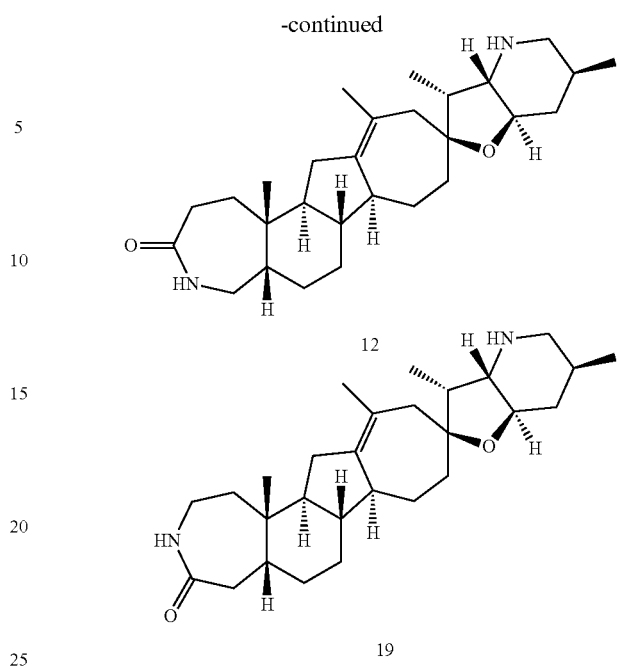

An ethanol solution (5 ml) of compound 17 (185 mg, 0.3 mmol, 1 eq) was treated with hydroxylamine hydrochloride (140 mg, 2 mmol, 6 eq), sodium acetate (160 mg, 2 mmol, 6 eq), and water (0.5 ml), and the mixture was stirred at rt for 1 hr. The mixture was split between EtOAc and water (50 ml each). The organic layer was washed with brine (30 ml), dried over sodium sulfate, and concentrated to a white residue. The crude product was purified by silica gel chromatography (ether/hexanes 2:3→1:1) to give 193 mg of oxime 18.

Step G

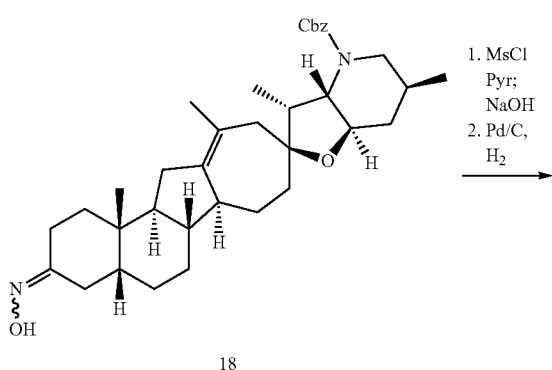

Compound 18 (50 mg, 0.087 mmol, 1.0 eq) was dissolved in dry pyridine (1.0 mL) and at 0° C. treated with methanesulfonyl chloride (20.0 mg, 0.174 mmol, 2.0 eq). After stirring for 2 h, the solution was warmed to rt and treated with 5N sodium hydroxide (0.3 ml, 1.5 mmol, 18 eq) and stirred for 1 h. The mixture was split between EtOAc (30 mL) and 1M aqueous hydrogen chloride (15 mL). The organic layer was washed with water, washed with brine, dried over sodium sulfate, and concentrated to a clear oil. The mixture of lactams was purified by silica gel chromatography (80-100% ethyl acetate/hexanes, then 1% methanol in ethyl acetate) to afford a mixture of the lactam regioisomers as a clear oil (34 mg, 68% yield).

The product carbamate lactams were dissolved in EtOAc (7 ml) in a flask with stir bar and rubber septum. The solution was sparged with nitrogen, and 10% Pd/C (wet, Degussa type E101, Aldrich, 25 mg) was added. This mixture was sparged with nitrogen and then hydrogen gas and stirred at rt for 3 h. The mixture was then sparged with nitrogen, filtered through a 0.45 μM polyethylene membrane and concentrated to a clear oil. The oil was purified by silica gel flash chromatography (0.5% ammonium hydroxide/2-20% MeOH/DCM), and the pure fractions were concentrated to give an oil that was lyophilized from 7% water/tbutanol, to afford a 1:1 mixture of unseparated lactams, as a white powder (19 mg: [M+H]=441.6 m/z).

Example 4

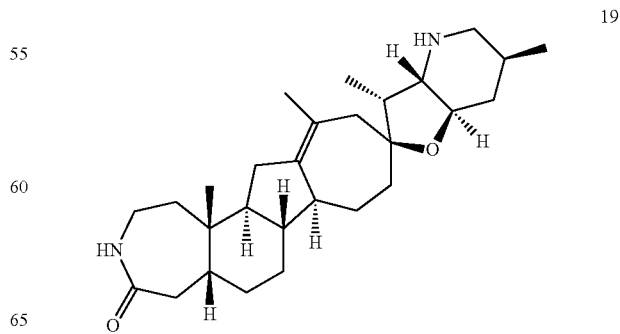

Compound 19 was made using procedures similar to those described in Example 3.

Example 5

Step A

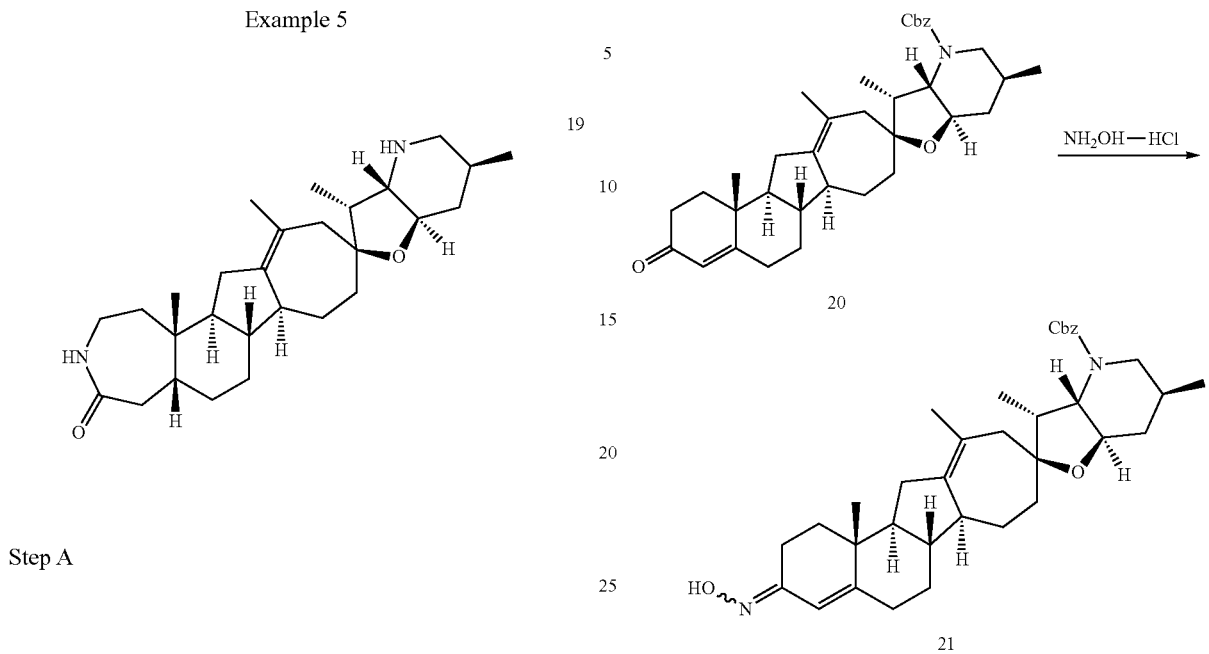

Compound 15 (2.0 g, 4.7 mmol, 1.0 eq) was dissolved in DCM (20.0 mL) and THF (20.0 mL) and at rt treated with triethylamine (3.3 ml, 23.6 mmol, 5.0 eq) and Cbz-Cl (0.73 ml, 5.2 mmol, 1.1 eq). 4-Dimethylaminopyridine (50 mg) was added, and the mixture was stirred for 60 min at rt. The mixture was split between EtOAc (200 mL) and 5% aqueous sodium bicarbonate (150 mL). The organic layer was washed with brine (50 mL), dried over sodium sulfate, and concentrated. Purification of the residue by silica gel flash chromatography (5→40% EtOAc/hexanes) afforded the desired carbamate as a white foam. (2.4 g).

Step B

Compound 20 (200.0 mg, 0.36 mmol, 1.0 eq) was dissolved in EtOH (3.0 mL) and water (0.3 mL) and at rt treated with hydroxylamine hydrochloride (150 mg, 2.1 mmol, 6.0 eq) and sodium acetate (176 mg, 2.1 mmol, 6 eq). The mixture was heated at 70° C. for 10 min. The mixture was split between EtOAc (30 mL) and water (15 mL). The organic layer was washed with brine (15 mL), dried over sodium sulfate, and concentrated to give the oxime 21 as a white foam. (202 mg).

Step C

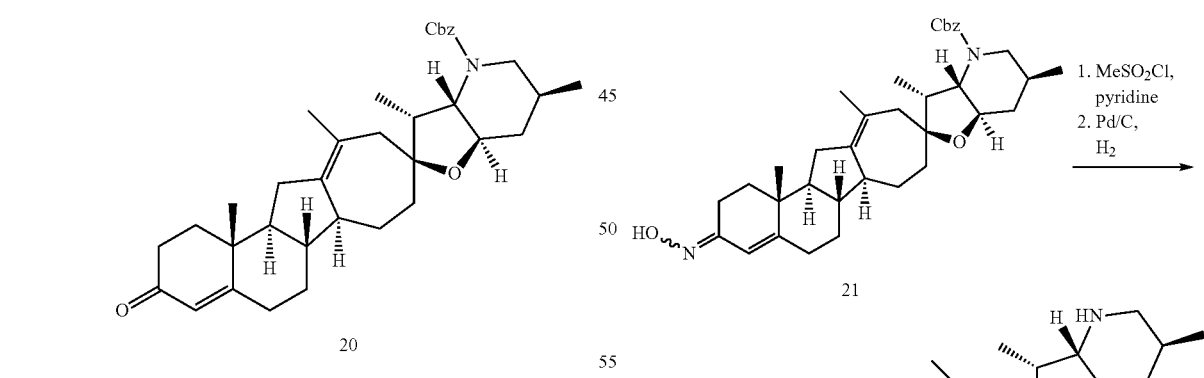

Compound 21 (200.0 mg, 0.34 mmol, 1.0 eq) was dissolved in dry pyridine (1.0 mL) and at 0° C. treated with methanesulfonyl chloride (120.0 mg, 1.05 mmol, 3.0 eq). After stirring for 2 h, the solution was warmed to rt and treated with 5 N sodium hydroxide (0.75 ml, 4.25 mmol, 12 eq) and stirred for 12 h. The mixture was split between EtOAc (30 mL) and 1 m aqueous HCl (15 mL). The organic layer was washed with water and then brine (15 mL each), dried over sodium sulfate, and concentrated to give the oxime O-methanesulfonate as a clear oil. This oil was suspended in MeOH (5 mL), treated with concentrated aqueous HCl (0.75 mL), and heated at 60° C. for 2 h. This dark brown mixture was concentrated in vacuo and purified by silica gel flash chromatography (50→100% EtOAc/hexanes followed by 1→5% MeOH in EtOAc) to give the unsaturated lactam as an isomerically pure white solid (45 mg).

The product carbamate lactam was dissolved in pyridine (7 mL) in a flask with stir bar and rubber septum. The solution was sparged with nitrogen, and 10% Pd/C (wet, Degussa type E101, Aldrich, 25 mg) was added. This mixture was sparged with nitrogen and then hydrogen gas and stirred at rt for 48 h. The mixture was then sparged with nitrogen, filtered through a 0.45 μm polyethylene membrane and concentrated to a clear oil. The oil was purified by silica gel chromatography (0.5% ammonium hydroxide/2→20% MeOH/DCM), and the pure fractions were concentrated to give an oil that was lyophilized from 7% water/t-butanol, affording the product as a white powder (14 mg: [M+H]=441.7 m/z).

Example 6

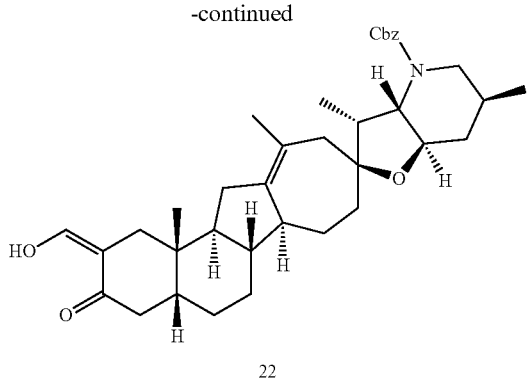

A dry round-bottom flask was charged with KOtBu (0.57 g, 5.1 mmol, 7 eq) and tBuOH (6 mL) and the solution was stirred at rt for 10 min. Compound 17 (0.3 g, 0.73 mmol, 1 eq) was added and stirred for 5 min. The white suspension became a yellow clear solution. Ethyl formate (0.35 mL, 4.4 mmol, 6 eq) was added dropwise, and the solution became slightly opaque and produced bubbles. The slurry was stirred at rt for 48 h. The mixture was then portioned between MTBE/1% NaOH (2×20 mL). The aqueous layer was acidified with 2 N HCl until the pH reached 5, then extracted with chloroform (2×). The combined organic layers were washed with water, dried over Na$_2$SO$_4$, and concentrated to dryness to give 200 mg pale yellow foam. This material was used without further purification in the next step.

Step B

A round-bottom flask was charged with compound 22 (2.0 g, 3.40 mmol, 1 eq) and was dissolved in toluene (25 mL). The reaction was charged with DDQ (0.849 g, 3.74 mmol, 1.1 eq). The mixture was stirred for 0.5 hr at rt. The reaction mixture was then concentrated in vacuo to 10% the original volume.

The residue was purified using silica gel flash chromatography (EtOAc/hexanes 10% 20%) to afford the desired material.

Step C

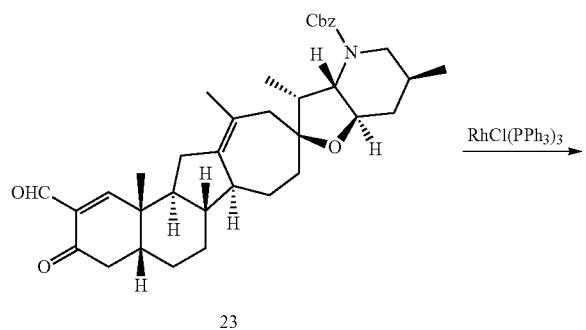

23

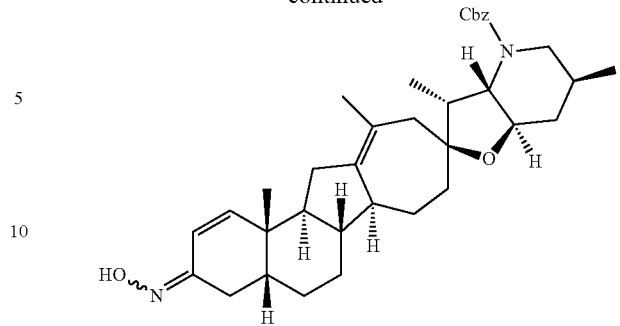

24

A round-bottom flask was charged with compound 23 (1.10 g, 1.88 mmol, 1 eq) and was dissolved in toluene (25 mL). The reaction was charged with Wilkinson's catalyst (1.77 g, 1.92 mmol, 1.02 eq). The mixture was heated to 80° C. stirred for 0.5 h. The reaction mixture was cooled and concentrated in vacuo to 10% the original volume. The residue was purified using silica gel flash chromatography (EtOAc/hexanes 10%→15%) to afford the desired material.

Step D

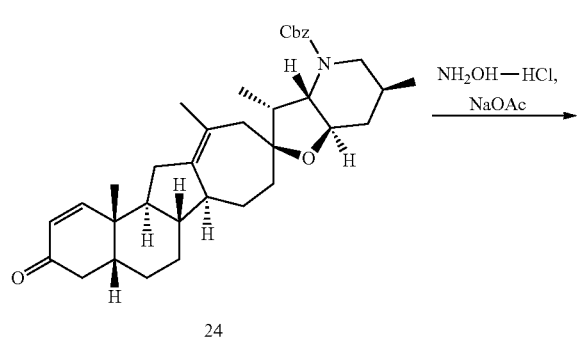

24

25

A round-bottom flask was charged with compound 24 (750 mg, 1.34 mmol, 1 eq) and was dissolved in EtOH (10 mL) and water (1 mL). The reaction was charged with hydroxylamine hydrochloride (662 mg, 8.07 mmol, 6.0 eq) and sodium acetate (561 mg, 8.07 mmol, 6 eq). The mixture was stirred for 0.5 h at rt. The reaction mixture was partitioned between water and EtOAc. The organic was separated, dried and concentrated to dryness. The residue was purified using silica gel flash chromatography (EtOAc/hexanes 10%→25%) to afford the desired material.

Step E

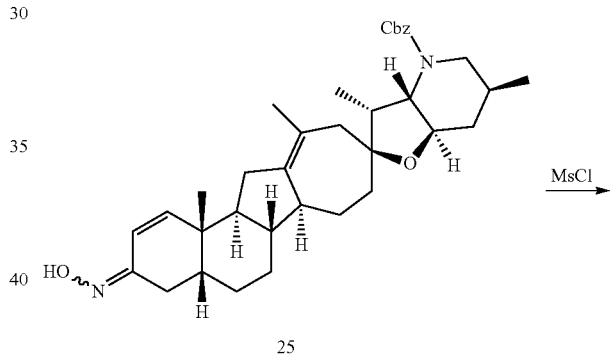

25

26

A round-bottom flask was charged with compound 25 (770 mg, 1.34 mmol, 1 eq) and was dissolved in pyridine (10 mL). The reaction was charged with methanesulfonylchloride (462 mg, 4.03 mmol, 3.0 eq). The mixture was stirred for 0.5 h at rt. The reaction mixture was partitioned between an aqueous solution of 1N HCl and EtOAc. The organic was separated, dried and concentrated to dryness. The residue was purified using silica gel flash chromatography (EtOAc/hexanes 15%→20%) to afford the desired material.

Step F

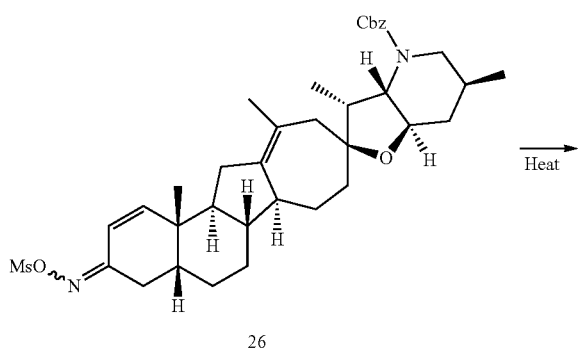

26

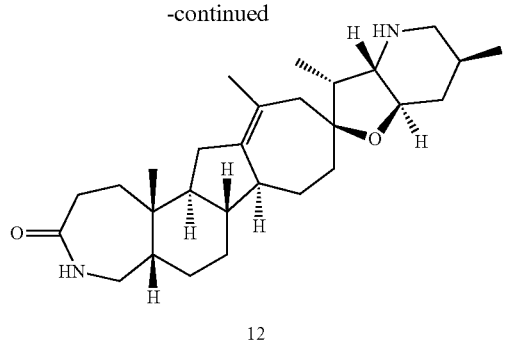

12

A round-bottom flask was charged with compound 27 (142 mg, 0.248 mmol, 1 eq) and 10% palladium on carbon (30 mg). The solids were suspended in EtOH (3 mL). The suspension was placed under hydrogen atmosphere and the mixture was stirred for 2 h at rt. The reaction mixture was filtered on celite and the filtrate concentrated to dryness. The residue was purified using silica gel flash chromatography (MeOH/DCM 0%→5%) to afford the desired material. ([M+H]=441.5 m/z).

Example 7

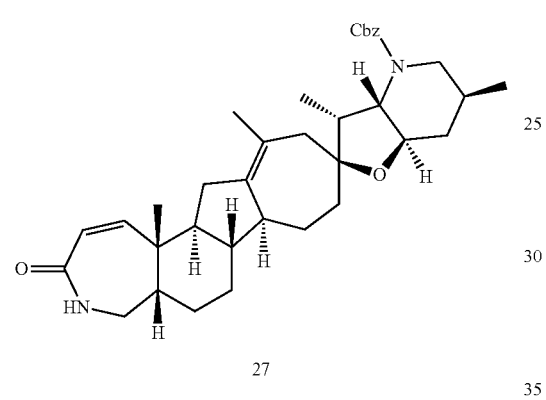

27

A round-bottom flask was charged with compound 26 (765 mg, 1.18 mmol, 1 eq) and was dissolved in MeOH (30 mL). The reaction was charged with concentrated HCl (300 mg, 3.54 mmol, 7.0 eq). The mixture was heated to 60° C. and stirred for 17 h. The reaction mixture was partitioned between a saturated aqueous solution of sodium bicarbonate and EtOAc. The organic was separated, dried and concentrated to dryness. The residue was purified using silica gel flash chromatography (EtOAc/hexanes 50% 90%) to afford the desired material.

Step G

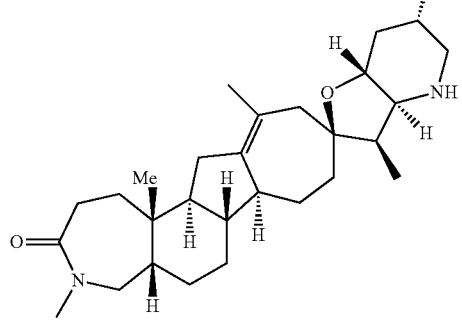

31

Step A

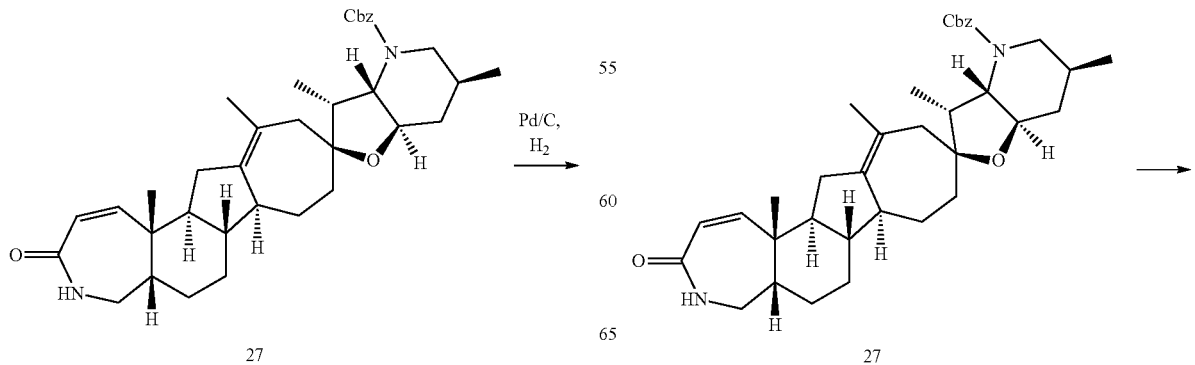

27

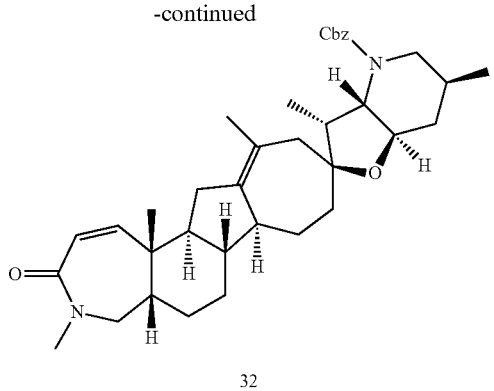

32

A round-bottom flask was charged with starting material (51 mg, 0.09 mmol, 1 eq). The solid was dissolved in 5 mL of tetrahydrofuran. The solution was cooled to −78° C. A 0.5M solution of potassium bis(trimethylsilyl)amide in toluene (0.207 mL, 0.104 mmol, 1.2 eq.) was charged and the solution was stirred for 0.5 hr at −78° C. The reaction was then charged with methyliodide (11 uL, 0.179 mmol, 2 eq.) and the reaction was warmed to 25° C. The reaction was stirred o/n then charged with water and ethyl acetate. The organic was separated, dried and concentrated to dryness. The residue was dissolved in DCM and was loaded onto a SiO₂. Elution with 50 to 90% EtOAc/hexanes gave Compound 32 ([M+H]= 587.8 m/z).
Step B

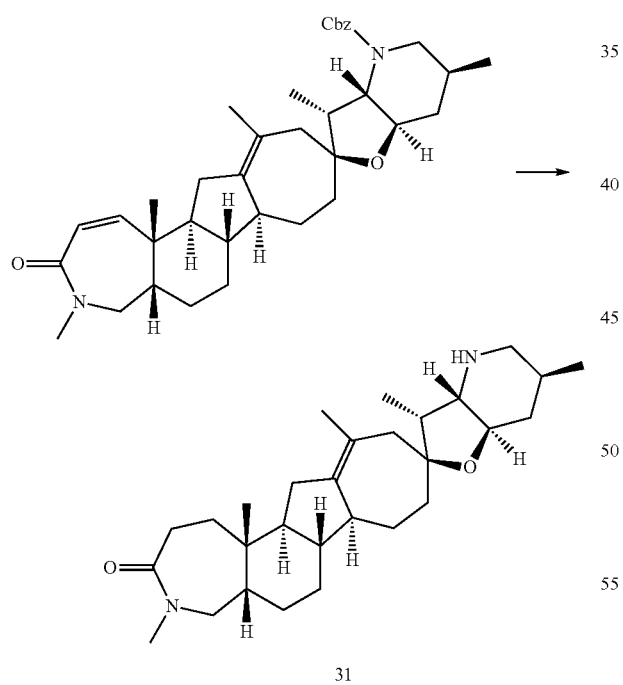

31

A round-bottom flask was charged with starting material (50 mg, 0.085 mmol, 1 eq) and 10% palladium on carbon (10 mg). The solids were suspended in 3 mL of ethanol. The suspension was placed under hydrogen atmosphere and the mixture was stirred for 4 hrs at 25° C. LCMS show complete disappearance of starting material. The reaction mixture was filtered on celite and the filtrate concentrated to dryness. The residue was dissolved in DCM and was loaded onto a SiO₂. Elution with 0 to 8% MeOH/DCM gave the desired product Compound 31 ([M+H]=455.5 m/z).

Example 8

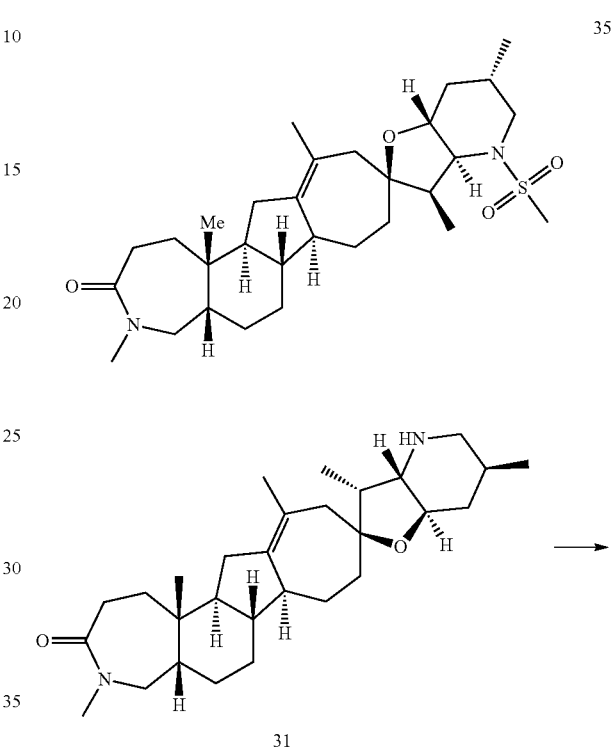

35

A round-bottom flask was charged with Compound 31 (10 mg, 0.022 mmol, 1 eq) and dichloromethane (1 mL). The solution was charged with triethylamine (3.2 uL, 0.066 mmol, 3 eq.) and methane sulfonylchloride (14 uL, 0.088 mmol, 4 eq.) were charged and the solution was stirred for 0.5 hr. The reaction mixture was partitioned between a solution a saturated aqueous solution of sodium bicarbonate and ethyl acetate. The organic was separated, dried and concentrated to dryness. The residue was dissolved in DCM and was loaded onto a SiO₂. Elution with 75 to 90% EtOAc/hexanes gave the desired material Compound 35 ([M+H]=533.8 m/z).

Example 9

Example 10

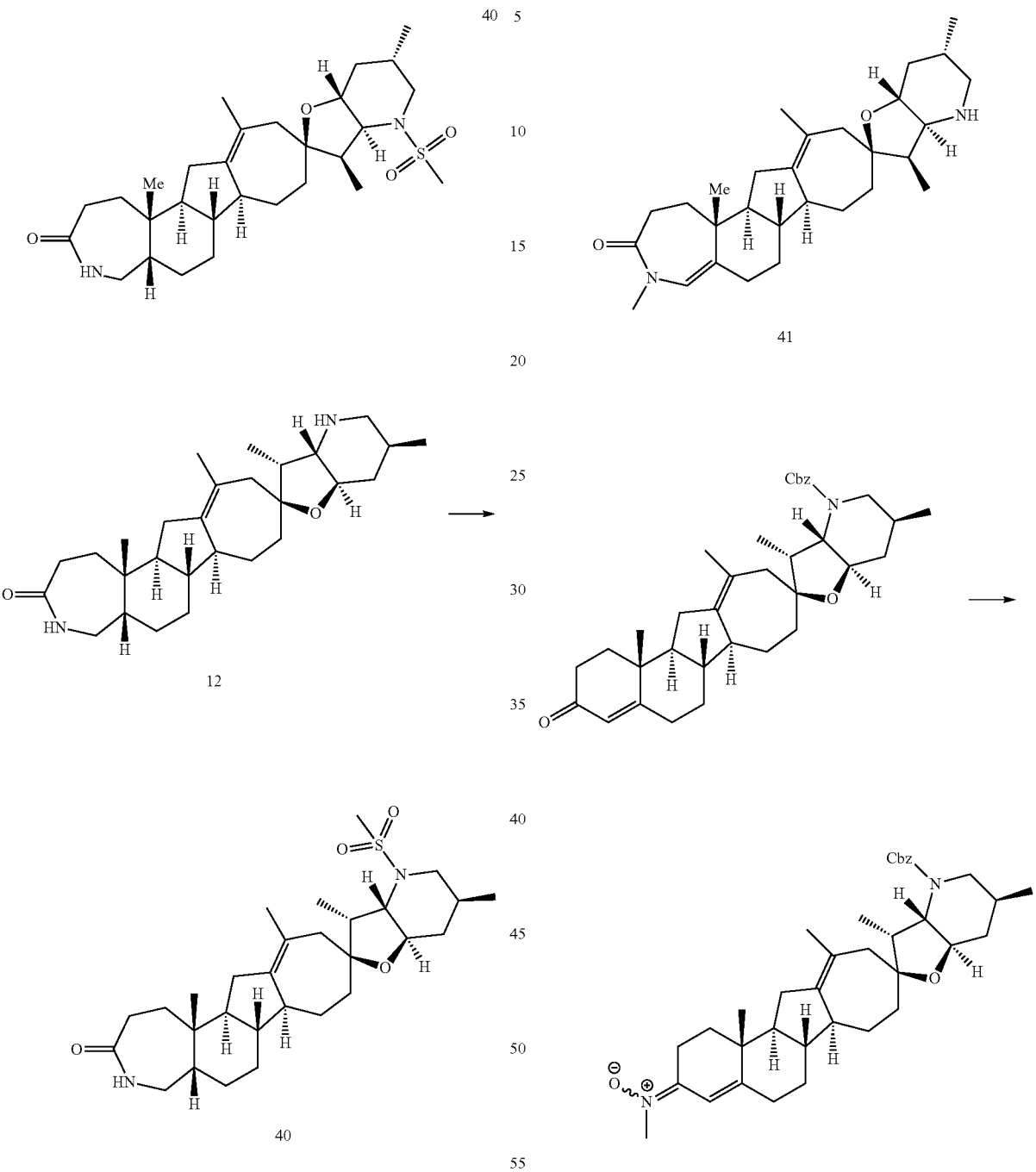

A round-bottom flask was charged with Compound 12 (16 mg, 0.036 mmol, 1 eq) and dichloromethane (1 mL). The solution was charged with triethylamine (8.0 uL, 0.109 mmol, 3 eq.) and methane sulfonylchloride (20 uL, 0.149 mmol, 4 eq.) were charged and the solution was stirred for 0.5 hr. The reaction mixture was partitioned between a solution a saturated aqueous solution of sodium bicarbonate and ethyl acetate. The organic was separated, dried and concentrated to dryness. The residue was dissolved in DCM and was loaded onto a SiO$_2$. Elution with 75 to 90% EtOAc/hexanes gave the desired material Compound 40 ([M+H]=519.8 m/z).

A round-bottom flask was charged with starting material (1.15 g, 2.06 mmol, 1 eq) and ethanol (15 mL). The solution was charged with sodium acetate (1.015 g, 12.37 mmol, 6 eq.) and N-methylhydroxylamine HCl (0.189 g, 2.27 mmol, 1.1 eq.) were charged and the solution was heated to 70° C. and stirred for 6 hrs. The reaction mixture was cooled to rt and concentrated. The residue was partitioned between water and ethyl acetate. The organic was separated, dried and concentrated to dryness. The residue was dissolved in DCM and was loaded onto a SiO$_2$. Elution with 0 to 10% MeOH/DCM gave the desired material ([M+H]=587.9 m/z).

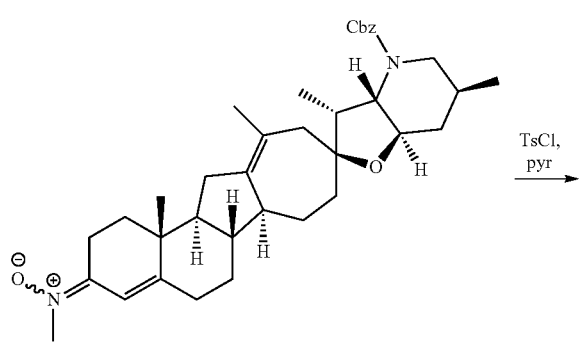

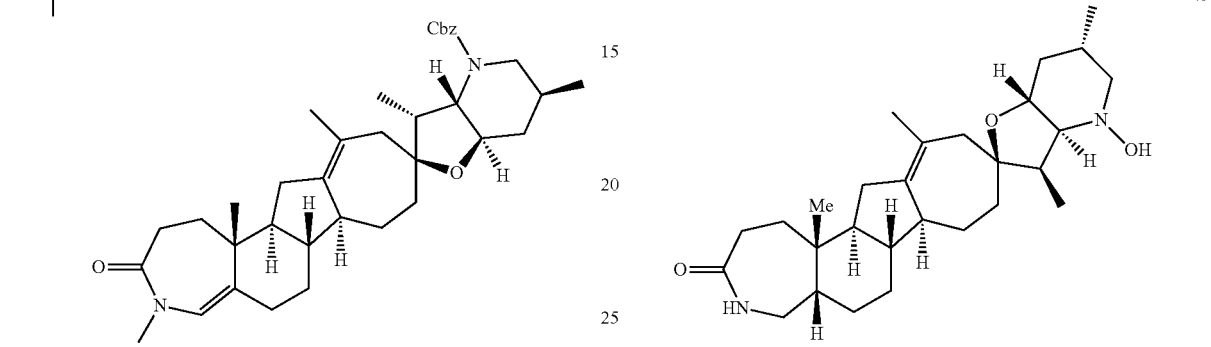

A round-bottom flask was charged with starting material (1.10 g, 1.875 mmol, 1 eq) and dissolved in pyridine (15 mL) and water (0.7 mL). The solution was charged with tosyl chloride (0.430 g, 2.249 mmol, 1.2 eq.) was charged and the solution the solution was stirred at rt for 0.5 hr. The reaction mixture was cooled to rt and concentrated. The residue was partitioned between water and MTBE. The organic was separated, dried and concentrated to dryness. The residue was dissolved in DCM and was loaded onto a SiO$_2$. Elution with 10 to 80% EtOAc/Hex gave the desired material ([M+H]= 587.9 m/z).

A round-bottom flask was charged with starting material (100 mg, 0.170 mmol, 1 eq) and 10% palladium on carbon (50 mg). The solids were suspended in 3 mL of ethyl acetate. The suspension was placed under hydrogen atmosphere and the mixture was stirred for 4 hrs at 25° C. The reaction mixture was filtered on celite and the filtrate concentrated to dryness. The residue was dissolved in DCM and was loaded onto a SiO$_2$. Elution with 0 to 10% MeOH/DCM gave the desired Compound 41 ([M+H]=453.5 m/z).

Example 11

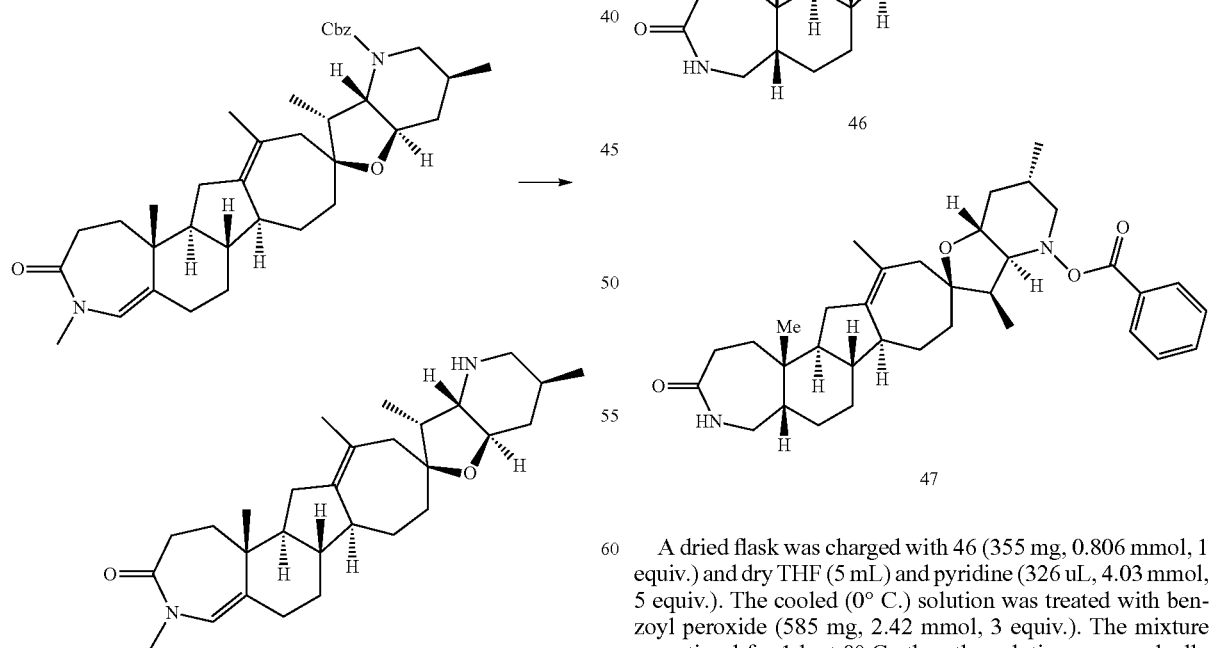

Step A

A dried flask was charged with 46 (355 mg, 0.806 mmol, 1 equiv.) and dry THF (5 mL) and pyridine (326 uL, 4.03 mmol, 5 equiv.). The cooled (0° C.) solution was treated with benzoyl peroxide (585 mg, 2.42 mmol, 3 equiv.). The mixture was stirred for 1 h at 0° C., then the solution was gradually warmed to 25° C. After 2 h, the mixture was diluted with EtOAc and washed with aqueous saturated NaHCO$_3$ solution. The aqueous layer was extracted once more with EtOAc. The combined organic layer were dried over $Na_2SO_4$, filtered, and evaporated to dryness. The oil was dissolved in $CH_2Cl_2$ and purified by $SiO_2$ column eluting with hexane/EtOAc (40 to 100%) to give 238 mg of desired compound 47.
Step B

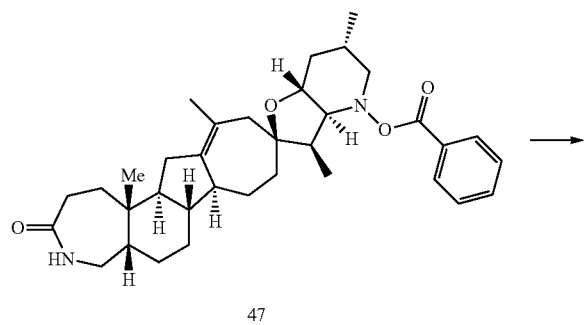

A round-bottom flask was charged with 47 (229 mg, 0.41 mmol, 1 equiv.) and MeOH (5 mL). The solution was treated at 25° C. in presence of 2 N KOH (1 mL, 2 mmol, 5 equiv.). The mixture was stirred for 3 h. The solvent was removed by nitrogen stream and the solution was neutralized with 500 uL of 1N HCl. The aqueous layer was extracted with three portions of $CH_2Cl_2$. Combined organic layers were dried over $Na_2SO_4$, filtered, and concentrated to dryness. The crude material (220 mg) was dissolved with $CH_2Cl_2$, loaded onto a $SiO_2$ column (12 g) and eluted with $CH_2Cl_2$/MeOH (0% to 100%) to give the hydroxylamine 45. The mterial recrystallized from heptane/2-propanol to give desired material 3 ([M+H]=547.5 m/z).

Compound 50 was prepared using techniques similar to those described above.

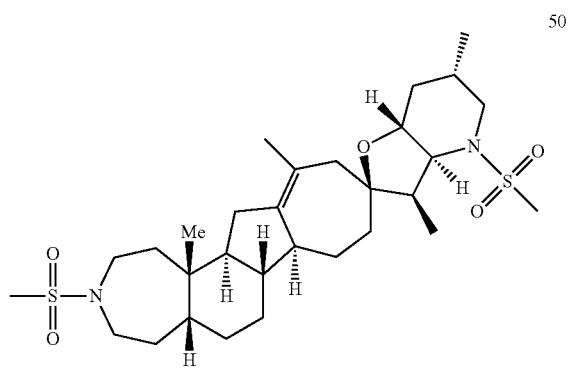

Example 12

Inhibition of the Hedgehog Pathway in Cell Culture Using Analogs of Cyclopamine Hedgehog pathway specific cancer cell killing effects may be ascertained using the following assay. C3H10T1/2 cells differentiate into osteoblasts when contacted with the sonic hedgehog peptide (Shh-N). Upon differentiation; these osteoblasts produce high levels of alkaline phosphatase (AP) which can be measured in an enzymatic assay (Nakamura, et al., BBRC (1997) 237:465). Compounds that block the differentiation of C3H10T1/2 into osteoblasts (a Shh dependent event) can therefore be identified by a reduction in AP production (van der Horst, et al., Bone (2003) 33:899). The assay details are described below. The results ($EC_{50}$ for inhibition) of the differentiation assay are shown below in Table 1.

Assay Protocol
Cell Culture

Mouse embryonic mesoderm fibroblasts C3H10T1/2 cells (obtained from ATCC) were cultured in Basal MEM Media (Gibco/Invitrogen) supplemented with 10% heat inactivated FBS (Hyclone), 50 units/ml penicillin and 50 ug/ml streptomycin (Gibco/Invitrogen) at 37° C. with 5% $CO_2$ in air atmosphere.

Alkaline Phosphatase Assay

C3H10T1/2 cells were plated in 96 wells with a density of $8 \times 10^3$ cells/well. Cells were grown to confluence (72 hrs). After sonic Hedgehog (250 ng/ml), and/or compound treatment, the cells were lysed in 110 μL, of lysis buffer (50 mM Tris pH 7.4, 0.1% Triton X 100), plates were sonicated and lysates spun through 0.2 μm PVDF plates (Corning). 40 μL of lysates was assayed for AP activity in alkaline buffer solution (Sigma) containing 1 mg/ml p-Nitrophenyl Phosphate. After incubating for 30 min at 37° C., the plates were read on an Envision plate reader at 405 nm. Total protein was quantified with a BCA protein assay kit from Pierce according to manufacturer's instructions. AP activity was normalized against total protein. Note that "A" indicates that the $IC_{50}$ is less than 20 nM, "B" indicates that the $IC_{50}$ is 20-100 nM, "C" indicates that the $IC_{50}$ is >100 nM.

TABLE 1

| Approximate $EC_{50}$ for Inhibition | |
|---|---|
| Compound | Differentiation Assay $EC_{50}$ |
| 1 | A |
| 11 | C |
| 12 | B |
| 19 | C |
| 31 | B |
| 35 | C |
| 40 | A |
| 41 | C |
| 50 | C |

Example 13

Pancreatic Cancer Model

The activity of Compound 12 was further tested in a human pancreatic model: BXPC-3 cells were implanted subcutaneously into the flanks of the right legs of mice. On day 42 post-tumor implant, the mice were randomized into two groups to receive either Vehicle (30% HPBCD) or Compound 12. Compound 12 was administered orally at 30 mg/kg/day. After receiving 25 daily doses, Compound 12 reduced tumor volume growth by 16% when compared to the vehicle control. At the end of the study, the tumors were harvested 4 hours post the last dose to evaluate an on target response by q-RT-PCR analysis of the HH pathway genes. Analysis of human Gli-1 resulted in no modulation. Analysis of murine Gli-1 mRNA levels resulted in a robust down-regulation in the Compound treated group, when compared to the Vehicle treated group. Inhibition of the hedgehog pathway in mouse cells, but not human tumor cells, indicates that one effect of the hedgehog inhibitor is to affect a tumor-stroma interaction.

Example 14

Medulloblastoma Model

The activity of Compound 12 was also evaluated in a transgenic mouse model of medulloblastoma. Mice that are heterozygous for loss of function mutations in the tumor suppressors Patched1 (Ptch1) and Hypermethylated in Cancer (Hic1) develop spontaneous medulloblastoma. Similar to human medulloblastoma, these tumors demonstrate complete promoter hypermethylation of the remaining Hic1 allele, as well as loss of expression of the wild type Ptch1 allele. When passaged as subcutaneous allografts, these tumors grow aggressively and are Hedgehog pathway-dependent. This model was employed to evaluate the efficacy of orally administered Compound, and to correlate activity with drug exposure in plasma and tumors. Oral administration (PO) of a single dose of Compound 12 led to dose-dependent down-regulation of the HH pathway in subcutaneously implanted tumors, as measured by decreased Gli-1 mRNA expression 8 hours post dose administration.

Daily (QD) administration of the Compound PO led to a dose dependent inhibition of tumor growth, with frank tumor regression seen at higher doses. The approximate effective daily oral dose for 50% inhibition of tumor growth (ED50) is between 3 and 7.5 mg/kg. This demonstrates that the hedgehog inhibitor Compound 12 inhibits both the hedgehog pathway and tumor growth in a tumor dependent on the hedgehog pathway due to a genetic mutation.

Example 15

Multiple Myeloma

The ability of Compound 12 to inhibit the growth of multiple myeloma cells (MM) in vitro was tested, using human multiple myeloma cells lines (NCI-H929 and KMS12) and primary clinical bone marrow specimens derived from patients with MM. The cells were treated for 96 hours with Compound, washed, then plated in methylcellulose. Tumor colonies were quantified 10-21 days later as an indicator of cell growth potential following treatment. Treatment of cell lines or primary patient specimens resulted in decreased cell growth compared to an untreated control. Where the untreated control showed 100% growth of cells, each of the treated cell lines, as well as the clinical samples, showed less than about 25% growth.

Example 16

Acute Myeloid Leukemia and Myelodysplastic Syndrome

The ability of Compound 12 to inhibit the in vitro growth of human cell lines derived from patients with acute myeloid leukemia (AML, cell line U937) and myelodysplastic syndrome (MDS, cell line KG1 and KG1a) was studied. Each of the cell lines was treated for 72 hours with Compound 12 (1.0 uM) followed by plating in methylcellulose. Growth of these cell lines was inhibited by Compound 12, as summarized in the table below.

TABLE 2

Inhibition of cell growth in AML and MDS

| | Disease | | |
| --- | --- | --- | --- |
| | AML | MDS | |
| Cell line | U937 | KG1 | KG1a |
| % colony formation with Compound 12 (relative to vehicle control) | 43.4 | 25.1 | 34.6 |

Example 17

Non-Hodgkin's Lymphoma (NHL) and Hodgkin's Disease (HD)

The ability of Compound 12 to inhibit the in vitro growth of human cell lines derived from patients with non-Hodgkin's lymphoma (cell lines RL and Jeko-1) and Hodgkin's disease (cell line L428) was studied. Each of the cell lines was treated for 72 hours with Compound 12 (1.0 uM) followed by plating in methylcellulose. Growth of these cell lines was inhibited by Compound 12, as summarized in the table below.

TABLE 3

Inhibition of cell growth in HD and NHL

| | Disease | | |
| --- | --- | --- | --- |
| | HD | NHL | |
| Cell line | L428 | RL | Jeko-1 |
| % colony formation with Compound 12 (relative to vehicle control) | 21.4 | 14.3 | 27.4 |

Example 18

Pre-B Cell Acute Lymphocytic Leukemia

The activity of Compound 12 (1 uM) against three pre-B cell acute lymphocytic leukemia cell lines (REH, RS4-11, and Nalm-6) was studied, using a transient transfection assay in which a Gli-reponsive luciferase reporter was transiently transfected into cells. Treatment with Compound 12 repressed luciferase activity compared to a vehicle treated control (Table 4). This demonstrates that Compound 12 is an effective antagonist of the hedgehog pathway.

TABLE 4

Repression of luciferase activity

| | Cell line | | |
|---|---|---|---|
| | REH | RS4-11 | Nalm-6 |
| Relative luc activity (vehicle alone) | 6.73 | 12.97 | 8.42 |
| Relative luc activity (+ Compound) | 1.12 | 1.31 | 1.44 |

The effect of Compound 12 on the growth of two of these cell lines, treated in vitro for 72 hours, was also studied. Following treatment, cells were washed and plated in methylcellulose. There was little inhibition of colony formation, but subsequent replating of colonies demonstrated a significant inhibition of cell growth (Table 5).

TABLE 5

Inhibition of cell growth in ALL

| | Cell line | |
|---|---|---|
| | REH | RS4-11 |
| % colony formation with Compound (relative to vehicle control) - 1° plating | 63 | 71 |
| % colony formation with Compound (relative to vehicle control) - 2° plating | 9 | 11 |

INCORPORATION BY REFERENCE

All of the U.S. patents and U.S. published patent applications cited herein are hereby incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

The invention claimed is:

1. A compound of the formula:

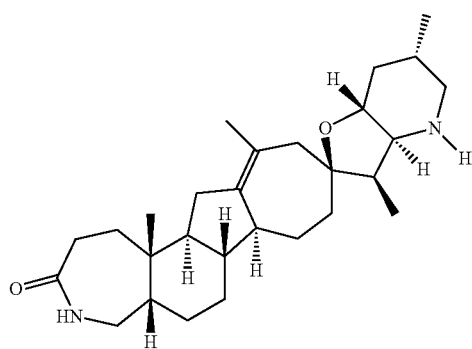

or a pharmaceutically acceptable salt thereof.

2. A pharmaceutical composition comprising a compound of the formula:

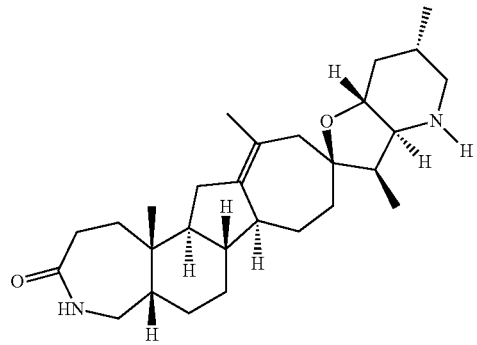

or a pharmaceutically acceptable salt thereof and at least one pharmaceutically acceptable excipient.

3. A method of treating cancer, which comprises administering to a subject in need thereof a therapeutically effective amount of a compound of the formula:

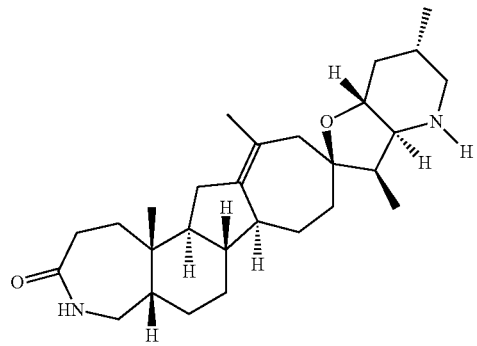

or a pharmaceutically acceptable salt thereof; wherein the cancer is selected from the group consisting of acute lymphocytic leukemia, acute myelocytic leukemia, basal cell carcinoma, bile duct carcinoma, bladder carcinoma, breast cancer, chondrosarcoma, chronic lymphocytic leukemia, chronic myeloid leukemia, colon cancer, esophageal cancer, gastric cancer, gastrointestinal stromal tumor, glioma, hepatocellular cancer, Hodgkin's disease, leukemia, lung cancer, medulloblastoma, melanoma, multiple myeloma, myelodysplastic syndrome, neuroectodermal tumors, non-Hodgkin's type lymphoma, osteogenic sarcoma, ovarian cancer, pancreatic cancer, prostate cancer, sarcoma, and testicular cancer.

4. The method of claim 3, wherein the cancer is selected from the group consisting of acute lymphocytic leukemia, basal cell carcinoma, breast cancer, chondrosarcoma, chronic lymphocytic leukemia, chronic myeloid leukemia, colon cancer, esophageal cancer, gastric cancer, glioma, hepatocellular cancer, lung cancer, medulloblastoma, multiple myeloma, non-Hodgkin's type lymphoma, osteogenic sarcoma, ovarian cancer, pancreatic cancer, and prostate cancer.

5. The method of claim 3, wherein the cancer is pancreatic cancer.

6. The method of claim 3, wherein the cancer is chondrosarcoma.

7. The method of claim 3, wherein the cancer is lung cancer.

8. The method of claim 7, wherein the lung cancer selected from the group consisting of small cell lung cancer and non-small cell lung cancer.

9. The method of claim 3, wherein the cancer is basal cell carcinoma.

10. The method of claim 3, wherein the cancer is medulloblastoma.

11. The method of claim 3, wherein the cancer is ovarian cancer.

12. The method according to claim 3, wherein the cancer is osteogenic sarcoma.

13. The method of claim 3, wherein the cancer is selected from the group consisting of acute lymphocytic leukemia, acute myelocytic leukemia, chronic lymphocytic leukemia, chronic myeloid leukemia, Hodgkin's disease, leukemia, multiple myeloma, myelodysplastic syndrome, and non-Hodgkin's type lymphoma.

14. The method of claim 3, wherein the cancer is selected from the group consisting of acute lymphocytic leukemia, acute myelocytic leukemia, chronic myelocytic leukemia, and chronic lymphocytic leukemia.

15. The method of claim 3, wherein the compound or pharmaceutically acceptable salt thereof is used in combination with one or more chemotherapeutic or other anti-cancer agent.

16. The method of claim 15, wherein the other anti-cancer agent is radiation.

17. The method of claim 3, wherein the compound is administered locally to a tumor.

18. The method of claim 3, wherein the compound is administered systemically.

19. The method of claim 3, wherein the mode of administration of said compound is inhalation, oral, intravenous, sublingual, ocular, transdermal, rectal, vaginal, topical, intramuscular, intraperitoneal, epidural, subcutaneous, buccal, or nasal.

20. The method of claim 19, wherein the mode of administration is oral, intravenous, or topical.

21. A method of inhibiting activation of a hedgehog pathway in a patient diagnosed with a hyperproliferative disorder, comprising administering to the patient a compound, or a pharmaceutically acceptable salt thereof, as claimed in claim 1 in an amount sufficient to reduce the activation of the hedgehog pathway in a cell of the patient.

22. The method of claim 21, wherein said hyper proliferative disorder is cancer.

23. A method of antagonizing the hedgehog pathway in a subject, the method comprising administering to the subject an effective amount of a compound, or a pharmaceutically acceptable salt thereof, as claimed in claim 1.

* * * * *

UNITED STATES PATENT AND TRADEMARK OFFICE
CERTIFICATE OF CORRECTION

PATENT NO. : 8,431,566 B2
APPLICATION NO. : 13/250080
DATED : April 30, 2013
INVENTOR(S) : Alfredo Castro et al.

It is certified that error appears in the above-identified patent and that said Letters Patent is hereby corrected as shown below:

Title Page, Col. 2 under item (56), (Other Publications), line 10, delete "Hedgehod" and insert -- "Hedgehog --

Title Page 2, Col. 1 under item (56), (Other Publications), line 11, delete "Ongogene" and insert -- Oncogene --

Title Page 2, Col. 1 under item (56), (Other Publications), line 16, delete "Hedgehod" and insert -- Hedgehog --

Title Page 2, Col. 1 under item (56), (Other Publications), line 28, delete "Hedgehod" and insert -- Hedgehog --

Title Page 2, Col. 2 under item (56), (Other Publications), line 35, delete "Expressionsl" and insert -- Expressions --

Title Page 2, Col. 2 under item (56), (Other Publications), line 57, delete "Holosprosencephaly" and insert -- Holoprosencephaly" --

Title Page 2, Col. 2 under item (56), (Other Publications), line 57, delete "1996" and insert -- (1996) --

Title Page 2, Col. 2 under item (56), (Other Publications), line 59, delete "at" and insert -- et --

Title Page 2, Col. 2 under item (56), (Other Publications), line 71, delete "Singallng" and insert -- signaling --

Title Page 2, Col. 2 under item (56), (Other Publications), line 71, delete "Zenograft" and insert -- Xenograft --

Title Page 3, Col. 1 under item (56), (Other Publications), line 1, delete "at" and insert -- et --

Signed and Sealed this
Eighteenth Day of February, 2014

Michelle K. Lee
*Deputy Director of the United States Patent and Trademark Office*

CERTIFICATE OF CORRECTION (continued)
U.S. Pat. No. 8,431,566 B2

Title Page 3, Col. 1 under item (56), (Other Publications), line 4, delete "thunbergll" and insert -- thunbergii --

Title Page 3, Col. 1 under item (56), (Other Publications), line 9, delete "at" and insert -- et --

Title Page 3, Col. 1 under item (56), (Other Publications), line 18, delete "(1953)" and insert -- (1963) --

Title Page 3, Col. 2 under item (56), (Other Publications), line 9, delete "chonrosarcoma" and insert -- chondrosarcoma --

Title Page 3, Col. 2 under item (56), (Other Publications), line 14, delete "Glil" and insert -- Glial --

Title Page 3, Col. 2 under item (56), (Other Publications), line 45, after "Diseases"," insert -- 2011 AACR Education --

In the Claims:

Col. 62, line 20-21, claim 22, delete "hyper proliferative" and insert -- hyperproliferative --